US009890369B2

(12) United States Patent
Bachran et al.

(10) Patent No.: US 9,890,369 B2
(45) Date of Patent: Feb. 13, 2018

(54) **CYTOLETHAL DISTENDING TOXIN SUBUNIT B CONJUGATED OR FUSED TO *BACILLUS ANTHRACIS* TOXIN LETHAL FACTOR**

(71) Applicant: The United States of America, as represented by the Secretary, Department of Health and Human Services, Washington, DC (US)

(72) Inventors: Christopher H. Bachran, Heidelberg (DE); Stephen H. Leppla, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/898,248

(22) PCT Filed: Jun. 19, 2014

(86) PCT No.: PCT/US2014/043131
§ 371 (c)(1),
(2) Date: Dec. 14, 2015

(87) PCT Pub. No.: WO2014/205187
PCT Pub. Date: Dec. 24, 2014

(65) Prior Publication Data
US 2016/0145590 A1    May 26, 2016

Related U.S. Application Data

(60) Provisional application No. 61/837,428, filed on Jun. 20, 2013.

(51) Int. Cl.
| | | |
|---|---|---|
| *C07K 14/32* | (2006.01) | |
| *C12N 9/22* | (2006.01) | |
| *C07K 14/285* | (2006.01) | |
| *A61K 38/16* | (2006.01) | |
| *A61K 38/46* | (2006.01) | |
| *A61K 38/48* | (2006.01) | |
| *C12N 9/54* | (2006.01) | |
| *A61K 47/64* | (2017.01) | |

(52) U.S. Cl.
CPC ............ *C12N 9/22* (2013.01); *A61K 38/164* (2013.01); *A61K 38/465* (2013.01); *A61K 38/4886* (2013.01); *A61K 47/6415* (2017.08); *C07K 14/285* (2013.01); *C07K 14/32* (2013.01); *C12N 9/54* (2013.01); *C12Y 301/21001* (2013.01); *C07K 2319/55* (2013.01); *C12Y 301/00* (2013.01); *C12Y 304/24083* (2013.01)

(58) Field of Classification Search
None
See application file for complete search history.

(56) References Cited

U.S. PATENT DOCUMENTS

| | | |
|---|---|---|
| 4,450,150 A | 5/1984 | Sidman |
| 4,816,567 A | 3/1989 | Cabilly et al. |
| 5,087,616 A | 2/1992 | Myers et al. |
| 5,225,539 A | 7/1993 | Winter |
| 5,242,824 A | 9/1993 | Hellstrom et al. |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,591,828 A | 1/1997 | Bosslet et al. |
| 5,639,641 A | 6/1997 | Pedersen et al. |
| 5,693,761 A | 12/1997 | Queen et al. |
| 5,714,352 A | 2/1998 | Jakobobits |
| 5,747,654 A | 5/1998 | Pastan et al. |
| 5,846,535 A | 12/1998 | Pastan et al. |
| 5,859,205 A | 1/1999 | Adair et al. |
| 5,888,773 A | 3/1999 | Jost et al. |
| 5,889,157 A | 3/1999 | Pastan et al. |
| 5,981,726 A | 11/1999 | Pastan et al. |
| 5,990,296 A | 11/1999 | Pastan et al. |
| 6,265,150 B1 | 7/2001 | Terstappen et al. |
| 6,558,672 B1 | 5/2003 | Pastan et al. |
| 7,081,518 B1 | 7/2006 | Pastan et al. |
| 7,355,012 B2 | 4/2008 | Pastan et al. |
| 7,368,110 B2 | 5/2008 | Pastan et al. |
| 7,470,775 B2 | 12/2008 | Pastan et al. |
| 7,494,812 B2 | 2/2009 | Zadeh |

(Continued)

FOREIGN PATENT DOCUMENTS

| | | |
|---|---|---|
| EP | 0 173 464 A2 | 3/1986 |
| EP | 0 404 097 A2 | 12/1990 |

(Continued)

OTHER PUBLICATIONS

International Bureau, International Search Report in Patent Application No. PCT/US2014/043131, dated Oct. 28, 2014.
International Bureau, Written Opinion in Patent Application No. PCT/US2014/043131, dated Oct. 28, 2014.
Arndt et al.: "Helix-stabilized fv (hsfv) antibody fragments: substituting the constant domains of a fab fragment for a heterodimeric coiled-coil domain," *J. Mol. Biol.*, 312: 221-228 (2001).
Arora et al., "Fusions of anthrax toxin lethal factor with shiga toxin and diphtheria toxin enzymatic domains are toxic to mammalian cells," *Infection and Immunity*, 62(11): 4955-4961 (1994).
Bachran et al., "Anthrax Toxin-Mediated Delivery of the Pseudomonas Exotoxin A Enzymatic Domain to the Cytosol of Tumor Cells via Cleavable Ubiquitin Fusions," *mBio*, 4(3): 201-213 (2013).

(Continued)

*Primary Examiner* — Brian Gangle
(74) *Attorney, Agent, or Firm* — Leydig, Voit & Mayer, Ltd.

(57) ABSTRACT

Disclosed is a protein comprising a cytolethal distending toxin subunit B (CdtB) conjugated or fused to a *Bacillus anthracis* toxin lethal factor (LF) or a functional portion of LF. Related chimeric molecules, as well as related nucleic acids, recombinant expression vectors, host cells, populations of cells, pharmaceutical compositions, methods of treating or preventing cancer, and methods of inhibiting the growth of a target cell are also disclosed.

20 Claims, 5 Drawing Sheets

(56) References Cited

U.S. PATENT DOCUMENTS

| | | | |
|---|---|---|---|
| 7,521,054 | B2 | 4/2009 | Pastan et al. |
| 7,541,034 | B1 | 6/2009 | Fitzgerald et al. |
| 8,460,660 | B2 | 6/2013 | Ho et al. |
| 2007/0189962 | A1 | 8/2007 | Pastan et al. |

FOREIGN PATENT DOCUMENTS

| | | |
|---|---|---|
| EP | 0 239 400 B1 | 8/1994 |
| GB | 2 188 638 A | 10/1987 |
| WO | WO 1987/002671 A1 | 5/1987 |
| WO | WO 1993/011161 A1 | 6/1993 |
| WO | WO 1998/045322 A2 | 10/1998 |
| WO | WO 03/027135 A2 | 4/2003 |
| WO | WO 2003/027135 A2 | 4/2003 |
| WO | WO 2009/032954 A1 | 3/2009 |
| WO | WO 2011/032022 A1 | 3/2011 |
| WO | WO 2012/139112 A1 | 10/2012 |

OTHER PUBLICATIONS

Bachran et al., "Cytolethal distending toxin B as a cell-killing component of tumor-tarueted anthrax toxin fusion proteins," *Cell Death and Disease*; 5(1) 1003 (2014).

Bachran et al., "Efficient tumor therapy by anthrax toxin fusion proteins that contain cytolethal distending toxin B," abstract of poster presented at 104th Annual Meeting of the American Association for Cancer Research (Mar. 6, 2013).

Bachran et al. "Efficient tumor therapy by anthrax toxin fusion proteins that contain cytolethal distending toxin B," poster presented at 104th Annual Meeting of the American Association for Cancer Research (Apr. 6-10, 2013).

Bachran et al., "Recombinant expression and purification of a tumor-targeted toxin in Bacillus anthracis," *Biochemical and Biophysical Research Communications*, 430(1): 150-155 (2013).

Davies et al., "Antibody VH Domains as Small Recognition Units," *Nat. Biotechnol.*, 13:475-479 (1995).

Frankel et al., "Targeted Toxins," *Ciln. Cancer Res.*, 6: 326-334 (2000).

Ghahroudi et al., "Selection and identification of single domain antibody fragments from camel heavy-chain antibodies," *FEBS Lett.*, 414:521-526 (1997).

Harmsen et al., "Properties, production, and applications of camelid single-domain antibody fragments," *Appl. Microbiol. Biotechnol.*, 77(1 ): 13-22 (2007).

Haskard et al, "The production of human monoclonal autoantibodies from patients with rheumatoid arthritis by the EBV-hybridoma technique," *J. Immunol. Methods*, 74(2), 361-67 (1984).

Holliger et al., "'Diabodies': small bivalet and bispecific antibody fragments," *Proc. Natl. Acad. Sci. USA*, 90: 6444-6448 (1993).

Holt et al., "Domain antibodies: proteins for therapy," *Trends Biotech*, 21(11):484-490 (2003).

Huse et al., "Generation of a large combinatorial library of the immunoglobulin repertoire in phage lambda," *Science*, 246, 1275-81 (1989).

Jones et al., "Replacing the complementarity-determining regions in a human antibody with those from a mouse," *Nature*, 321:522-524 (1986).

Köhler et al., "Derivation of specific antibody-producing tissue culture and tumor lines by cell fusion," *Eur. J. Immunol.*, 5: 511-519 (1976).

Kreitman, "Immunotoxins for targeted cancer therapy," *AAPS Journal*, 8(3): E532-E551 (2006).

Lauwereys et al., "Potent enzyme inhibitors derived from dromedary heavy-chain antibodies," *EMBO J*, 17:3512-3520 (1998).

Liu et al., "Tumor Cell-selective Cytotoxicity of Matrix Metalloproteinase-activated Anthrax Toxin," *Cancer Res.*, 60(21): 6061-67 (2000).

Liu et al., "Characterization of the interaction between anthrax toxin and its cellular receptors," *Cell. Microbiol.*, 9 977-87 (2007).

Liu et al., "Targeting of Tumor Cells by Cell Surface Urokinase Plasminogen Activator-dependent Anthrax Toxin," *J. Biol. Chem.*, 276(21): 17976-84 (2001).

Liu et al., "Intermolecular complementation achieves high-specificity tumor targeting, by anthrax toxin," *Nat. Biotechnol.*, 23(6): 725-30 (2005).

Liu et al., "Potent antitumor activity of a urokinase-activated engineered anthrax toxin," *Proc. Natl. Acad, Sci. USA*, 100(2): 657-62 (2003).

Mossoba et al., "Pentostatin Pius Cyclophosphamide Safely and Effectively Prevents Immunotoxin Immunogenicity in Murine Hosts," *Clin Cancer Res*, 17:3697-3705 (2011).

Mufson, "Tumor antigen targets and tumor immunotherapy." *Front. Biosci.*, 11:337-43 (2006).

Park et al., "Optimized Production and Purification of *Bacillus anthracic* Lethal Factor," *Protein Expression and Purification*, 18: 293-302 (2000).

Pedersen et al., "Comparison of Surface Accessible Residues in Human and Murine Immunoglobulin Fv Domains: Implication for Humanization of Murine Antibodies," *J. Mol, Biol.*, 235: 959-973 (1994).

Phillips et al., "Engineering Anthrax Toxin Variants That Exclusively Form Octamers and Their Application to Targeting Tumors," *J. Biol. Chem.*, 288(13): 9058-65 (2013).

Pomerantsev et al., "A Bacillus anthracia strain deleted for six proteases serves as an effective host for production of recombinant proteins" *Protein Expression and Purification*, 80: 80-90 (2011).

Reiter et al., "An antibody single-domain phage display library of a native heavy chain variable region: isolation of functional single-domain VH molecules with a unique interface," *J. Mol. Biol.* 290: 685-698 (1999).

Riechmann et al., "Reshaping human antibodies for therapy," *Nature*, 332: 323-327 (1988).

Roder et al., "The EBV-hybridoma technique," *Methods Enzymol.*, 121: 140-67 (1986).

Saerens et al., "Single-domain antibodies as building blocks for novel therapeutics," *Curr. Opin. Pharmacol.*, 8(5):600-608 (2008).

Verhoeyen et al, "Reshaping human antibodies: grafting an antilysozyme activity," *Science*, 239: 1534-36 (1988).

Wadhwa et al., "Receptor Mediated Glycotargeting," *J. Drug Targeting*, 3: 111-127 (1995).

Wesolowski et al., "Single domain antibodies: promising experimental and therapeutic tools in infection and immunity," *Med Microbiol Immunol.*, 198(3): 157-74 (2009).

Winter et al., "Man-made antibodies," *Nature*, 349: 293-299 (1991).

Genbank Accession No. M22589.1, 3 pages,1988.

Ho et al. "A novel high-affinity human monoclonal antibody to mesothelin" *Int J Cancer*, 128(9) 2020-2030 (2011).

Mikesell et al. "Evidence for Plasmid-Mediated Toxin Production in *Bacillus Anthracis*" *Infect and Immun*, 39(1) 371-376 (Jan. 1983).

Okinaka et al. "Sequence and Organization of pXO1, the Large *Bacillus anthracis* Plasmid Harboring the Anthrax Toxin Genes" *J. Bacteriol.* 181(20) 6509-6515 (Oct. 1999).

Singh et al. "A deleted variant of *Bacillus anthracis* protective antigen is non-toxic and blocks anthrax toxin action in Vivo" *J. Bio. Chem.* 264(32) 19103-19107 (1989).

Vodkin et al. "Cloning of protective antigen gene of *Bacillus anthracis*" *Cell* 34, 693-597 (Sep. 1983).

Welkos et al. "Sequence and analysis of the DNA encoding protective antigen of *Bacillus anthracis*" *Gene*, 69, 287-300 (1988).

Chowdhury et al. "Isolation of Anti-Mesothelin Antibodies from a Phage Display Library", *Molecular Immunology*, vol. 34, No. 1, pp. 9-20 (1997).

Hassan et al., "Preclinical Evaluation of MORAB-009, a Chimeric Antibody Targeting Tumor-Associated Mesothelin," *Cancer Immunity*, vol. 7, pp. 20 (2007).

Hollevoet et al., "Methylation-Associated Partial Down-Regulation of Mesothelin Causes Resistance of Anti-Mesothelin Immunotoxins in a Pancreatic Cancer Cell Line," *PLOS Once*, DOI:10137 (2015).

Onda et al., "New Monoclonal Antibodies to Mesothelin Useful for Immunohistochemistry, Fluorescence-Activated Cell Sorting, Western Blotting, and Elisa", *Clin Cancer Res*, 11(16) (2005).

CYTOLETHAL DISTENDING TOXIN SUBUNIT B CONJUGATED OR FUSED TO *BACILLUS ANTHRACIS* TOXIN LETHAL FACTOR

CROSS-REFERENCE TO RELATED APPLICATIONS

This patent application is a U.S. National Phase of International Patent Application No. PCT/US2014/043131, filed Jun. 19, 2014, which claims the benefit of U.S. Provisional Patent Application No. 61/837,428, filed Jun. 20, 2013, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,059 Byte ASCII (Text) file named "722621_ST25.TXT," dated Dec. 10, 2015.

BACKGROUND OF THE INVENTION

Cytolethal distending toxin (Cdt) is a bacterial toxin with cytotoxic activity. Accordingly, Cdt and portions thereof may be effective for destroying or inhibiting the growth of undesirable cells, such as cancer cells. Cdt and portions thereof may, therefore, be useful for treating or preventing diseases related to the growth of undesirable cells. Nevertheless, there are obstacles to the effective use of Cdt and portions thereof to inhibit the growth of cells. For example, inefficient delivery of Cdt and portions thereof to the interior of the cell may lessen the cytotoxic effects. Accordingly, there is a need for improved Cdt and portions thereof.

BRIEF SUMMARY OF THE INVENTION

Disclosed is a protein comprising a cytolethal distending toxin subunit B (CdtB) conjugated or fused to a *Bacillus anthracis* toxin lethal factor (LF) or a functional portion of LF. The protein possesses an improved ability to transit to the interior of a target cell. Related chimeric molecules, as well as related nucleic acids, recombinant expression vectors, host cells, populations of cells, pharmaceutical compositions, methods of treating or preventing a condition, and methods of inhibiting the growth of a target cell are also disclosed.

An embodiment of the invention provides a protein comprising a cytolethal distending toxin subunit B (CdtB) conjugated or fused to a *Bacillus anthracis* toxin lethal factor (LF) or a functional portion of LF.

Additional embodiments of the invention provide related chimeric molecules, as well as related nucleic acids, recombinant expression vectors, host cells, populations of cells, and pharmaceutical compositions.

Still another embodiment of the invention provides a method of treating or preventing a condition in a mammal comprising administering the inventive protein, chimeric molecule, nucleic acid, recombinant expression vector, host cell, population of cells, or pharmaceutical composition, to the mammal in an amount effective to treat or prevent the condition in the mammal.

Another embodiment of the invention provides a method of inhibiting the growth of a target cell, the method comprising contacting the cell with the inventive protein, chimeric molecule, nucleic acid, recombinant expression vector, host cell, population of cells, or pharmaceutical composition, in an amount effective to inhibit growth of the target cell.

Additional embodiments of the invention provide methods of producing the inventive protein and methods of producing the inventive chimeric molecule.

DETAILED DESCRIPTION OF THE INVENTION

Figure 1:
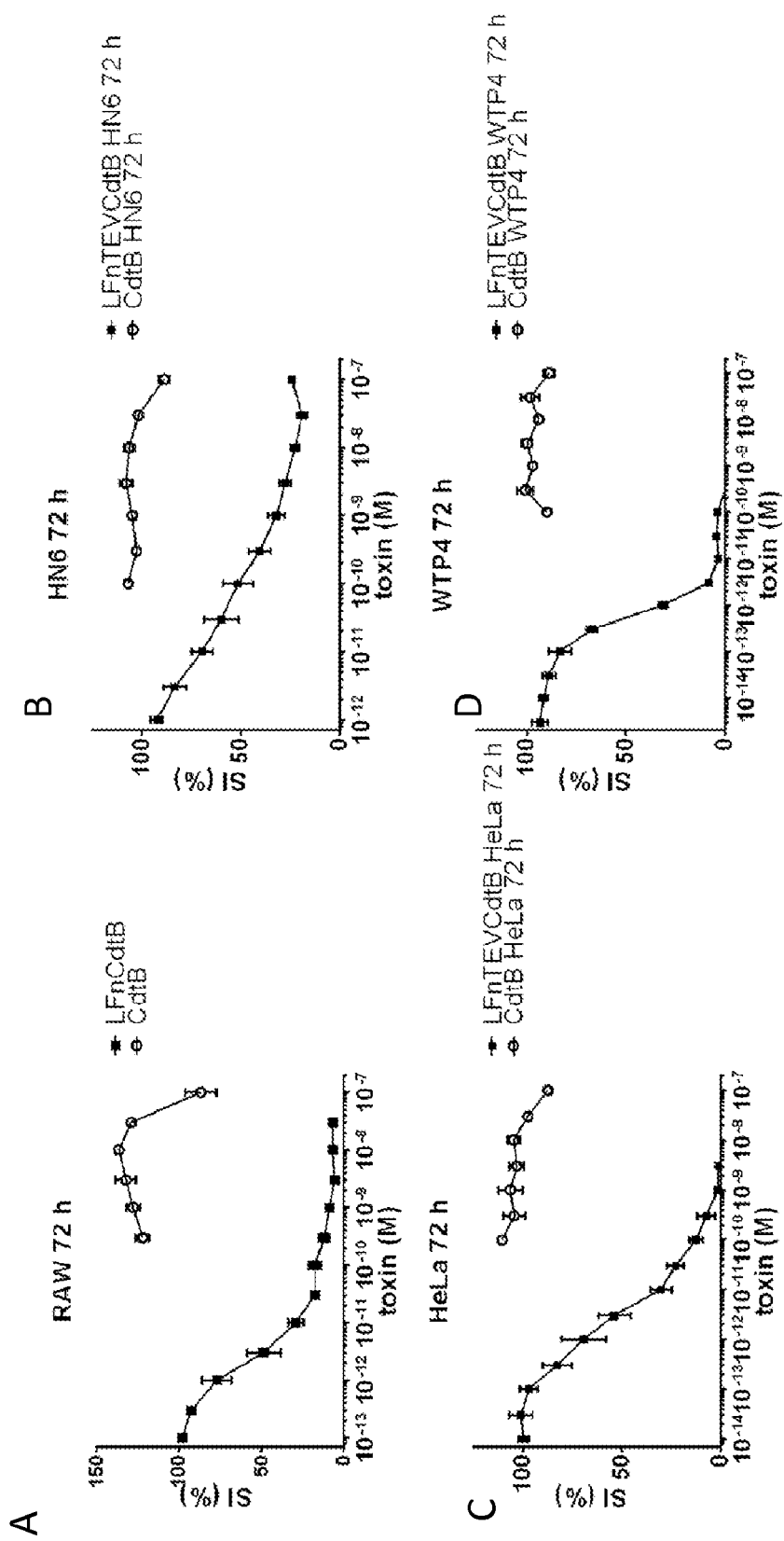
FIGS. 1A-1D are graphs showing the survival index (SI) (percentage) of RAW264.7 (A), HN6 (B), HeLa (C), or WTP4 CHO K1 (D) cells treated with protective antigen (PA) and varying concentrations of cytolethal distending toxin subunit B (CdtB) (circles) or a protein comprising CdtB conjugated or fused to *Bacillus anthracis* toxin lethal factor (LFn) (LFnCdtB) (squares).

It has been discovered that the delivery of cytolethal distending toxin subunit B (CdtB) to the interior of a target cell may be improved by conjugating or fusing the CdtB to *Bacillus anthracis* toxin lethal factor (LF). Accordingly, an embodiment of the invention provides a protein comprising a CdtB conjugated or fused to a LF or a functional portion of LF.

CdtB is the catalytic subunit of the bacterial toxin cytolethal distending toxin (Cdt). Without being bound by a particular theory or mechanism, it is believed that the cytotoxic activity of CdtB occurs through the degradation of nuclear DNA in host cells, inducing G2/M cell cycle arrest, inducing apoptosis, by reducing intracellular levels of plasma membrane-associated signal molecule phosphatidylinositol-3,4,5-triphosphate (PIP3), or combinations thereof. The inventive proteins may comprise CdtB from any suitable species. In an embodiment of the invention, the CdtB comprises *Haemophilus ducreyi* CdtB (SEQ ID NO: 1), *Escherichia coli* CdtB (SEQ ID NO: 11), *Actinobacillus* sp. CdtB (SEQ ID NO: 12), *Campylobacter jejuni* CdtB (SEQ ID NO: 13), *Aggregatibacter actinomycetemcomitans* CdtB (SEQ ID NO: 14), *Salmonella enterica* subsp. *enterica* serovar *Typhi* CdtB (SEQ ID NO: 15), *Helicobacter bilis* CdtB (SEQ ID NO: 16), *Providencia alcalifaciens* CdtB (SEQ ID NO: 17), or *Shigella dysenteriae* CdtB. In a preferred embodiment, the CdtB comprises *Haemophilus*

*ducreyi* CdtB (SEQ ID NO: 1). Alternatively, the CdtB may comprise a functional portion of CdtB. The "functional portion" of CdtB may include any portion of CdtB that retains cytotoxic activity. In reference to the parent CdtB, the functional portion can comprise, for instance, about 10%, 25%, 30%, 50%, 68%, 80%, 90%, 95%, or more, of the parent CdtB.

The CdtB is conjugated or fused to *Bacillus anthracis* toxin lethal factor (LF). LF is a component of the anthrax toxin produced by *Bacillus anthracis*. The LF may, advantageously, facilitate delivery of the CdtB to the interior of the cell in the presence of a *Bacillus anthracis* protective antigen (PA), including wild-type PA or any variant thereof. As used herein, the term "protective antigen" or "PA" refers to wild-type *Bacillus anthracis* PA and variants thereof, unless specified otherwise. PA is a component of anthrax toxin that may mediate translocation of the inventive proteins across the target cell membrane. Without being bound by a particular theory or mechanism, it is believed that PA binds to cell receptors and that the LF of the inventive protein binds to PA to form a complex. It is also believed that the complex is endocytosed, thereby translocating the inventive protein into the cytosol.

The LF of the inventive protein may comprise LF or a functional portion of LF. The "functional portion" of LF may include any portion of LF that retains the ability to bind to PA. In an embodiment of the invention, the LF comprises the N-terminal 255 amino acids of *Bacillus anthracis* LF (LFn). In this regard, the LF comprises SEQ ID NO: 2. In reference to the parent LF, the functional portion can comprise, for instance, about 10%, 25%, 30%, 50%, 68%, 80%, 90%, 95%, or more, of the parent LF.

In an embodiment of the invention, the CdtB is conjugated or fused directly to LF without any intervening moiety. In another embodiment, the CdtB is conjugated or fused to LF indirectly through a linker. The linker may be any agent or molecule that connects the CdtB to the LF. One of ordinary skill in the art recognizes that sites on the CdtB and LF, which are not necessary for the function of the inventive protein, may be ideal sites for attaching a linker, provided that the linker, once attached to the inventive protein, do(es) not interfere with the function of the inventive protein, i.e., cytotoxic activity, inhibition of growth of a target cell, or to treat or prevent cancer. The linker may be capable of forming covalent bonds to both the CdtB and the LF. Suitable linkers are known in the art and include, but are not limited to, straight or branched-chain carbon linkers, heterocyclic carbon linkers, and peptide linkers. The linker may be joined to amino acids through side groups (e.g., through a disulfide linkage to cysteine). Preferably, the linker is joined to the alpha carbon of the amino and carboxyl groups of the terminal amino acids. In an embodiment, the linker is a peptide linker comprising SEQ ID NO: 4.

In a preferred embodiment, the protein comprising CdtB conjugated or fused to LF through a linker peptide comprises SEQ ID NO: 3. The CdtB, LF, and linker (if present) may be arranged within the protein in any suitable order. In an embodiment, the LF is positioned on the N-terminus of the protein, and the CdtB is positioned on the C-terminus of the protein, without a linker in between the LF and the CdtB. In another embodiment of the invention, the LF is positioned on the N-terminus, the CdtB is positioned on the C-terminus, and the linker is positioned between the CdtB and the LF.

The inventive proteins provide many advantages. For example, the LF may, advantageously, facilitate delivery of the CdtB to the interior of the cell in the presence of a PA. Accordingly, higher amounts of CdtB may be delivered to the interior of a target cell using the inventive CdtB materials as compared to CdtB that is not conjugated or fused to LF. Greater cytotoxicity of target cells may, therefore, be achieved using lower dosages of the inventive CdtB materials as compared to the cytotoxicity achieved with CdtB that is not conjugated or fused to LF. In addition, the inventive CdtB materials may, advantageously, provide cytotoxic activity with little or no systemic toxicity, side effects, or combinations thereof.

Another embodiment of the invention provides a chimeric molecule comprising (a) (i) a targeting moiety, (ii) a *Bacillus anthracis* protective antigen (PA), or (iii) both (i) and (ii) conjugated or fused to (b) any of the inventive proteins described herein. The practice of conjugating and fusing compounds, e.g., inventive proteins, to targeting moieties and other compounds is known in the art. See, for instance, Wadwa et al., *J. Drug Targeting*, 3: 111 (1995), and U.S. Pat. No. 5,087,616.

In an embodiment, the chimeric molecule comprises a PA conjugated or fused to any of the inventive proteins described herein without a targeting moiety. The PA may be conjugated or fused to the inventive protein directly or indirectly through a linker. The linker that connects the inventive protein to the PA may be as described herein with respect to other aspects of the invention. The PA of the chimeric molecule may be any PA known in the art, including wild-type PA and variants thereof. Exemplary PAs may include any one or more of wild-type *Bacillus anthracis* PA (wtPA), PA-L1, PA-U2, PA-U7, PA-D512K, PA-GN, PA-NS, PA-R200A, and PA-I210A. See, for instance, Liu et al., *Cancer Res.*, 60(21): 6061-67 (2000); Liu et al., *J. Biol. Chem.*, 276(21): 17976-84 (2001); Liu et al., *Proc. Natl. Acad. Sci. USA*, 100(2): 657-62 (2003); Phillips et al., *J. Biol. Chem.*, 288(13): 9058-65 (2013); and Liu et al., *Nat. Biotechnol.*, 23(6): 725-30 (2005).

In another embodiment of the invention, the chimeric molecule comprises (a) a targeting moiety conjugated or fused to (b) any of the inventive proteins described herein without a PA. The targeting moiety may be conjugated or fused to the inventive protein directly or indirectly through a linker. The linker that connects the inventive protein to the targeting moiety may be as described herein with respect to other aspects of the invention.

Another embodiment of the invention provides a chimeric molecule comprising (a) a targeting moiety and a *Bacillus anthracis* protective antigen (PA) conjugated or fused to (b) any of the inventive proteins described herein. In this regard, the chimeric molecule may comprise a targeting moiety conjugated or fused to a PA which may, in turn, be conjugated or fused to the protein. The targeting moiety may be conjugated or fused to the PA directly or indirectly through a linker. The PA may be conjugated or fused to the protein directly or indirectly through a linker. The PA, targeting moiety, and linker may be as described herein with respect to other aspects of the invention. The PA, targeting moiety, and inventive protein may be arranged in any order within the chimeric molecule. In an embodiment of the invention, the PA is positioned between the targeting moiety and the inventive protein. In another embodiment of the invention, the targeting moiety is positioned between the PA and the inventive protein. In still another embodiment of the invention, the inventive protein is positioned between the PA and the targeting moiety.

Without being bound to a particular theory or mechanism, the inventive chimeric molecules including a PA recognize and specifically bind to a PA cell surface receptor (e.g., CMG2), thereby delivering the cytotoxic protein to the population of cells expressing the PA cell surface receptor with minimal or no cross-reactivity with cells that do not express the PA cell surface receptor.

While the PA may have a targeting function, the term "targeting moiety" as used herein, refers to any molecule or agent other than a PA that specifically recognizes and binds to a cell-surface marker, such that the targeting moiety directs the delivery of the inventive protein to a population of cells on which surface the receptor is expressed. Targeting moieties include, but are not limited to, antibodies (e.g., monoclonal antibodies), or fragments thereof, peptides, hormones, growth factors, cytokines, and any other natural or non-natural ligands.

The term "antibody," as used herein, refers to whole (also known as "intact") antibodies or antigen binding portions thereof that retain antigen recognition and binding capability. The antibody or antigen binding portions thereof can be a naturally-occurring antibody or antigen binding portion thereof, e.g., an antibody or antigen binding portion thereof isolated, purified, or both isolated and purified from a mammal, e.g., mouse, rabbit, goat, horse, chicken, hamster, human, etc. The antibody or antigen binding portion thereof can be in monomeric or polymeric form. Also, the antibody or antigen binding portion thereof can have any level of affinity or avidity for the cell surface marker. Desirably, the antibody or antigen binding portion thereof is specific for the cell surface marker, such that there is minimal cross-reaction with other peptides or proteins.

The antibody may be monoclonal or polyclonal and of any isotype, e.g., IgM, IgG (e.g. IgG, IgG2, IgG3 or IgG4), IgD, IgA or IgE. Complementarity determining regions (CDRs) of an antibody or single chain variable fragments (Fvs) of an antibody against a target cell surface marker can be grafted or engineered into an antibody of choice to confer specificity for the target cell surface marker upon that antibody. For example, the CDRs of an antibody against a target cell surface marker can be grafted onto a human antibody framework of a known three dimensional structure (see, e.g., International Patent Application Publications WO 1998/045322 and WO 1987/002671; U.S. Pat. Nos. 5,859,205; 5,585,089; and 4,816,567; European Patent Application Publication 0173494; Jones et al., *Nature*, 321: 522 (1986); Verhoeyen et al., *Science*, 239: 1534 (1988), Riechmann et al., *Nature*, 332: 323 (1988); and Winter & Milstein, *Nature*, 349: 293 (1991)) to form an antibody that may raise little or no immunogenic response when administered to a human. In a preferred embodiment, the targeting moiety is a monoclonal antibody.

The antigen binding portion can be any portion that has at least one antigen binding site, such as, e.g., the variable regions or CDRs of the intact antibody. Examples of antigen binding portions of antibodies include, but are not limited to, a heavy chain, a light chain, a variable or constant region of a heavy or light chain, a single chain variable fragment (scFv), or an Fc, Fab, Fab', Fv, or F(ab)$_2$' fragment; single domain antibodies (see, e.g., Wesolowski, *Med Microbiol Immunol.*, 198(3): 157-74 (2009); Saerens et al., *Curr. Opin. Pharmacol.*, 8(5):6 00-8 (2008); Harmsen and de Haard, *Appl. Microbiol. Biotechnol.*, 77(1): 13-22 (2007), helix-stabilized antibodies (see, e.g., Arndt et al., *J. Mol. Biol.*, 312: 221-228 (2001); triabodies; diabodies (European Patent Application Publication 0404097; International Patent Application Publication WO 1993/011161; and Hollinger et al., *Proc. Natl. Acad. Sci. USA,* 90: 6444-6448 (1993)); single-chain antibody molecules ("scFvs," see, e.g., U.S. Pat. No. 5,888,773); disulfide stabilized antibodies ("dsFvs," see, e.g., U.S. Pat. Nos. 5,747,654 and 6,558,672), and domain antibodies ("dAbs," see, e.g., Holt et al., *Trends Biotech,* 21(11):484-490 (2003), Ghahroudi et al., *FEBS Lett.,* 414:521-526 (1997), Lauwereys et al., *EMBO J* 17:3512-3520 (1998), Reiter et al., *J. Mol. Biol.* 290:685-698 (1999); and Davies and Riechmann, *Biotechnology,* 13:475-479 (2001)).

Methods of testing antibodies or antigen binding portions thereof for the ability to bind to any cell surface marker are known in the art and include any antibody-antigen binding assay, such as, for example, radioimmunoassay (RIA), ELISA, Western blot, immunoprecipitation, and competitive inhibition assays (see, e.g., Janeway et al., infra).

Suitable methods of making antibodies are known in the art. For instance, standard hybridoma methods are described in, e.g., Köhler and Milstein, *Eur. J. Immunol.,* 5, 511-519 (1976), Harlow and Lane (eds.), *Antibodies: A Laboratory Manual,* CSH Press (1988), and C. A. Janeway et al. (eds.), *Immunobiology,* 8$^{th}$ Ed., Garland Publishing, New York, N.Y. (2011)). Alternatively, other methods, such as EBV-hybridoma methods (Haskard and Archer, *J. Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352.

Phage display also can be used to generate the antibody that may be used in the chimeric molecules of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual,* 4th Edition, Cold Spring Harbor Laboratory Press, New York (2012)). Phages encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Alternatively, antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Alternatively, the antibody can be a genetically-engineered antibody, e.g., a humanized antibody or a chimeric antibody. Humanized antibodies advantageously provide a lower risk of side effects and can remain in the circulation longer. Methods for generating humanized antibodies are known in the art and are described in detail in, for example, Janeway et al., supra, U.S. Pat. Nos. 5,225,539, 5,585,089 and 5,693,761, European Patent 0239400 B1, and United Kingdom Patent 2188638. Humanized antibodies can also be generated using the antibody resurfacing technology described in, for example, U.S. Pat. No. 5,639,641 and Pedersen et al., *J. Mol. Biol.,* 235, 959-973 (1994).

The targeting moiety may specifically bind to any suitable cell surface marker. The choice of a particular targeting moiety, cell surface marker, or combinations thereof may be chosen depending on the particular cell population to be targeted. Cell surface markers are known in the art (see, e.g., Mufson et al., *Front. Biosci.,* 11:337-43 (2006); Frankel et al., *Clin. Cancer Res.,* 6:326-334 (2000); and Kreitman et al., *AAPS Journal,* 8(3): E532-E551 (2006)) and may be, for example, a protein or a carbohydrate. In an embodiment of the invention, the targeting moiety is a ligand that specifically binds to a receptor on a cell surface. Exemplary ligands include, but are not limited to, vascular endothelial growth factor (VEGF) or VEGF receptor, estrogen receptor, Fas, TNF-related apoptosis-inducing ligand (TRAIL), a cytokine (e.g., IL-2, IL-3, IL-15, IL-4, IL-13) and receptors thereof, a lymphokine, a hormone, and a growth factor (e.g., transforming growth factor (TGFa), neuronal growth factor, epidermal growth factor).

The cell surface marker can be, for example, a cancer antigen. The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

Exemplary cancer antigens to which the targeting moiety may specifically bind include, but are not limited to mucin 1 (MUC1), melanoma associated antigen (MAGE), preferentially expressed antigen of melanoma (PRAME), carcinoembryonic antigen (CEA), prostate-specific antigen (PSA), prostate specific membrane antigen (PSMA), granulocyte-macrophage colony-stimulating factor receptor (GM-CSFR), CD56, human epidermal growth factor receptor 2 (HER2/neu) (also known as erbB-2), CD5, CD7, tyrosinase tumor antigen, tyrosinase related protein (TRP)1, TRP2, NY-ESO-1, telomerase, p53, cluster of differentiation (CD) 19, CD21, CD22, CD25, CD30, CD33, CD79b, CD123, epidermal growth factor receptor variant III (EGFRvIII), interleukin-15 receptor, interleukin-8 receptor, interleukin-2 receptor, transferrin receptor, EGF receptor, mesothelin, cadherin, and Lewis Y. Mesothelin is expressed in, e.g., ovarian cancer, mesothelioma, non-small cell lung cancer, lung adenocarcinoma, fallopian tube cancer, head and neck cancer, cervical cancer, and pancreatic cancer. CD22 is expressed in, e.g., hairy cell leukemia, chronic lymphocytic leukemia (CLL), prolymphocytic leukemia (PLL), non-Hodgkin's lymphoma, small lymphocytic lymphoma (SLL), and acute lymphatic leukemia (ALL). CD25 is expressed in, e.g., leukemias and lymphomas, including hairy cell leukemia and Hodgkin's lymphoma. Lewis Y antigen is expressed in, e.g., bladder cancer, breast cancer, ovarian cancer, colorectal cancer, esophageal cancer, gastric cancer, lung cancer, and pancreatic cancer. CD33 is expressed in, e.g., acute myeloid leukemia (AML), chronic myelomonocytic leukemia (CML), and myeloproliferative disorders.

In an embodiment, the cell surface marker can be, for example, a human immunodeficiency virus (HIV) antigen. The term "HIV antigen" as used herein refers to any molecule (e.g., protein, peptide, lipid, carbohydrate, etc.) solely or predominantly expressed or over-expressed by an HIV-infected cell, such that the antigen is associated with the HIV-infected cell. The HIV antigen can additionally be expressed by cells that are not HIV-infected. However, in such cases, the expression of the HIV antigen by normal, non-HIV-infected cells is not as robust as the expression by the HIV-infected cells. In this regard, the HIV-infected cells can over-express the antigen or express the antigen at a significantly higher level, as compared to the expression of the antigen by normal, non-HIV-infected cells. In an embodiment, the HIV antigen is CD4, gp160, gp120, HIV-1 gag (p24), or gp41.

In an embodiment of the invention, the targeting moiety is an antibody that specifically binds to a cancer antigen. Exemplary antibodies that specifically bind to cancer antigens include, but are not limited to, antibodies against the transferrin receptor (e.g., HB21 and variants thereof), antibodies against CD22 (e.g., RFB4 and variants thereof), antibodies against CD25 (e.g., anti-Tac and variants thereof), antibodies against mesothelin (e.g., SS1, MORAb-009, SS, HN1, HN2, MN, MB, and variants thereof) and antibodies against Lewis Y antigen (e.g., B3 and variants thereof). In this regard, the targeting moiety may be an antibody selected from the group consisting of B3, RFB4, SS, SS1, MN, MB, HN1, HN2, HB21, and MORAb-009, and antigen binding portions thereof. Further exemplary targeting moieties suitable for use in the inventive chimeric molecules are disclosed e.g., in U.S. Pat. No. 5,242,824 (anti-transferrin receptor); U.S. Pat. No. 5,846,535 (anti-CD25); U.S. Pat. No. 5,889,157 (anti-Lewis Y); U.S. Pat. No. 5,981,726 (anti-Lewis Y); U.S. Pat. No. 5,990,296 (anti-Lewis Y); U.S. Pat. No. 7,081,518 (anti-mesothelin); U.S. Pat. No. 7,355,012 (anti-CD22 and anti-CD25); U.S. Pat. No. 7,368,110 (anti-mesothelin); U.S. Pat. No. 7,470, 775 (anti-CD30); U.S. Pat. No. 7,521,054 (anti-CD25); and U.S. Pat. No. 7,541,034 (anti-CD22); U.S. Patent Application Publication 2007/0189962 (anti-CD22); Frankel et al., *Clin. Cancer Res.,* 6: 326-334 (2000), and Kreitman et al., *AAPS Journal,* 8(3): E532-E551 (2006), each of which is incorporated herein by reference. In another embodiment, the targeting moiety may include the targeting moiety of immunotoxins known in the art. Exemplary immunotoxins include, but are not limited to, LMB-2 (Anti-Tac(Fv)-PE38), BL22 and HA22 (RFB4(dsFv)-PE38), SS1P (SS 1 (dsFv)-PE38), HB21-PE40, and variants thereof. In a preferred embodiment, the targeting moiety is the antigen binding portion of HA22. HA22 comprises a disulfide-linked Fv anti-CD22 antibody fragment conjugated to PE38. HA22 and variants thereof are disclosed in International Patent Application Publications WO 2003/027135 and WO 2009/032954, which are incorporated herein by reference.

Included in the scope of the invention are functional variants of the inventive proteins and chimeric molecules described herein. The term "functional variant" as used herein refers to a protein or chimeric molecule having substantial or significant sequence identity or similarity to a parent protein or chimeric molecule, which functional variant retains the biological activity of the protein or chimeric molecule of which it is a variant. Functional variants encompass, for example, those variants of the protein or chimeric molecule described herein (the parent protein or chimeric molecule) that retain the ability to kill target cells to a similar extent, the same extent, or to a higher extent, as the parent protein or chimeric molecule. In reference to the parent protein or chimeric molecule, the functional variant can, for instance, be at least about 30%, 50%, 75%, 80%, 90%, 98% or more identical in amino acid sequence to the parent protein or chimeric molecule.

The functional variant can, for example, comprise the amino acid sequence of the parent protein or chimeric molecule with at least one conservative amino acid substitution. Conservative amino acid substitutions are known in the art, and include amino acid substitutions in which one amino acid having certain physical properties, chemical properties, or combinations thereof is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. The protein or chimeric molecule can consist essentially of the specified amino acid sequence or sequences described herein, such that other components of the functional variant, e.g., other amino acids, do not materially change the biological activity of the functional variant.

The proteins and chimeric molecules of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

An embodiment of the invention provides a method of producing the inventive protein comprising (a) recombinantly expressing the protein and (b) purifying the protein. The proteins and chimeric molecules of the invention (including functional portions and functional variants thereof) can be obtained by methods known in the art. Suitable methods of de novo synthesizing proteins and chimeric molecules are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, proteins and chimeric molecules can be recombinantly produced using the nucleic acids described herein using standard recombinant methods. See, for instance, Sambrook et al., supra; and Ausubel et al., *Current Protocols in Molecular Biology*, Greene Publishing Associates and John Wiley & Sons, NY, 1994. Alternatively, the proteins and chimeric molecules described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive proteins and chimeric molecules can be synthetic, recombinant, isolated, purified, or combinations thereof.

The method further comprises purifying the protein. Once expressed, the inventive proteins may be purified in accordance with purification techniques known in the art. Exemplary purification techniques include, but are not limited to, ammonium sulfate precipitation, affinity columns, and column chromatography, or by procedures described in, e.g., R. Scopes, *Protein Purification*, Springer-Verlag, NY (1982).

Another embodiment of the invention provides a method of producing the inventive chimeric molecule comprising (a) recombinantly expressing the chimeric molecule and (b) purifying the chimeric molecule. The chimeric molecule may be recombinantly expressed and purified as described herein with respect to other aspects of the invention. In an embodiment of the invention, recombinantly expressing the chimeric molecule comprises inserting (a) (i) a nucleotide sequence encoding a targeting moiety, (ii) a nucleotide sequence encoding a PA, or (iii) both (i) and (ii) and (b) a nucleotide sequence encoding a protein into a vector. The method may comprise inserting (a) (i) the nucleotide sequence encoding the targeting moiety, (ii) a nucleotide sequence encoding a PA, or (iii) both (i) and (ii) and (b) the nucleotide sequence encoding the protein in frame so that it encodes one continuous polypeptide including (a) (i) a functional targeting moiety region, (ii) a functional PA region, or (iii) both (i) and (ii) and (b) a functional protein region. In an embodiment of the invention, the method comprises ligating (a) a nucleotide sequence encoding the protein to (b) (i) a nucleotide sequence encoding a targeting moiety, (ii) a nucleotide sequence encoding a PA, or (iii) both (i) and (ii) so that, upon expression, the protein is located at the carboxyl terminus of (i) the targeting moiety, (ii) PA, or (iii) both (i) and (ii). In an alternative embodiment, the method comprises ligating (a) a nucleotide sequence encoding the protein to (b) (i) a nucleotide sequence encoding a targeting moiety, (ii) a nucleotide sequence encoding a PA, or (iii) both (i) and (ii) so that, upon expression, the protein is located at the amino terminus of (i) the targeting moiety, (ii) PA, or (iii) both (i) and (ii).

Still another embodiment of the invention provides a method of producing the inventive chimeric molecule comprising (a) recombinantly expressing the inventive protein, (b) purifying the protein, and (c) covalently linking (i) a targeting moiety, (ii) a PA, or (iii) both (i) and (ii) to the purified protein. The inventive protein may be recombinantly expressed as described herein with respect to other aspects of the invention. The method further comprises covalently linking (a) (i) a targeting moiety, (ii) a PA, or (iii) both (i) and (ii) to (b) the purified protein. The method of attaching (a) a protein to (b) (i) a targeting moiety, (ii) a PA, or (iii) both (i) and (ii) may vary according to the chemical structure of the (i) targeting moiety, (ii) the PA, or (iii) both (i) and (ii). For example, the method may comprise reacting any one or more of a variety of functional groups e.g., carboxylic acid (COOH), free amine (—$NH_2$), or sulfhydryl (—SH) groups present on the protein with a suitable functional group on the (i) targeting moiety, (ii) the PA, or (iii) both (i) and (ii), thereby forming a covalent bind between the protein and (i) the targeting moiety, (ii) the PA, or (iii) both (i) and (ii). Alternatively or additionally, the method may comprise derivatizing (i) the targeting moiety, (ii) PA, or (iii) both (i) and (ii) or protein to expose or to attach additional reactive functional groups. Derivatizing may also include attaching one or more linkers to the protein or (i) the targeting moiety, (ii) PA, or (iii) both (i) and (ii).

In another embodiment of the invention, the inventive proteins and chimeric molecules may be produced using non-recombinant methods. For example, the inventive proteins and chimeric molecules described herein (including functional portions and functional variants) can be commercially synthesized by companies, such as Synpep (Dublin, Calif.), Peptide Technologies Corp. (Gaithersburg, Md.), and Multiple Peptide Systems (San Diego, Calif.). In this respect, the inventive proteins and chimeric molecules can be synthetic, recombinant, isolated, purified, or combinations thereof.

It may be desirable, in some circumstances, to free the protein from (i) the targeting moiety, (ii) PA, or (iii) both (i) and (ii) when the chimeric molecule has reached one or more target cells. In this regard, the inventive chimeric molecules may comprise a cleavable linker. The linker may be cleavable by any suitable means, e.g., enzymatically. For example, when the target cell is a cancer (e.g., tumor) cell, the chimeric molecule may include a linker cleavable under conditions present at the tumor site (e.g., when exposed to tumor-associated enzymes or acidic pH).

An embodiment of the invention provides a nucleic acid comprising a nucleotide sequence encoding any of the inventive proteins or the inventive chimeric molecules described herein. In an embodiment, the nucleic acid comprises a nucleotide sequence encoding LFn comprising SEQ ID NO: 7. In an embodiment, the nucleic acid comprises a nucleotide sequence encoding CdtB comprising SEQ ID NO: 8. In an embodiment, the nucleic acid comprises a nucleotide sequence encoding a linker comprising SEQ ID NO: 9. Preferably, the nucleic acid comprises a nucleotide sequence comprising both SEQ ID NOs: 7 and 8. In an especially preferred embodiment, the nucleic acid comprises a nucleotide sequence comprising all of SEQ ID NOs: 7-9.

The term "nucleic acid," as used herein, includes "polynucleotide," "oligonucleotide," and "nucleic acid molecule," and generally means a polymer of DNA or RNA, which can be single-stranded or double-stranded, which can be synthesized or obtained (e.g., isolated, purified, or both isolated and purified) from natural sources, which can contain natural, non-natural or altered nucleotides, and which can contain a natural, non-natural, or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, substitutions, or combinations thereof. However, it may be suitable in some instances, as discussed herein, for the nucleic acid to comprise one or more insertions, deletions, inversions, substitutions, or combinations thereof.

Preferably, the nucleic acids of the invention are recombinant. As used herein, the term "recombinant" refers to (i) molecules that are constructed outside living cells by joining natural or synthetic nucleic acid segments, or (ii) molecules that result from the replication of those described in (i) above. For purposes herein, the replication can be in vitro replication or in vivo replication.

The nucleic acids can be constructed based on chemical synthesis, enzymatic ligation reactions, or combinations thereof using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches, from a random sequence that happened to have only a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt conditions, high temperature conditions, or combinations thereof, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive proteins or chimeric molecules. It is generally appreciated that conditions can be rendered more stringent by the addition of increasing amounts of formamide.

The invention also provides a nucleic acid comprising a nucleotide sequence that is about 70% or more, e.g., about 80% or more, about 90% or more, about 91% or more, about 92% or more, about 93% or more, about 94% or more, about 95% or more, about 96% or more, about 97% or more, about 98% or more, or about 99% or more identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, which can be synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or for both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM, and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive protein or chimeric molecule (including functional portions and functional variants), or to the nucleotide sequence which is complementary to or which hybridizes to the nucleotide sequence encoding the protein or chimeric molecule. The selection of promoters, e.g., strong, weak, inducible, tissue-specific, and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell, an adherent cell or a suspended cell, i.e., a cell that grows in suspension. For purposes of producing a recombinant inventive protein or chimeric molecule, the host cell is preferably a prokaryotic cell, e.g., an E. coli cell.

Also provided by the invention is a population of cells comprising at least one host cell described herein. The population of cells can be a heterogeneous population comprising the host cell comprising any of the recombinant expression vectors described, in addition to at least one other cell, e.g., a host cell which does not comprise any of the recombinant expression vectors. Alternatively, the population of cells can be a substantially homogeneous population, in which the population comprises mainly (e.g., consisting essentially of) host cells comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population of host cells comprising a recombinant expression vector as described herein.

The inventive proteins, chimeric molecules (including functional portions and functional variants), nucleic acids, recombinant expression vectors, host cells, and populations of cells can be isolated, purified, or both isolated or purified. The term "isolated" as used herein means having been removed from its natural environment. The term "purified" as used herein means having been increased in purity, wherein "purity" is a relative term, and not to be necessarily construed as absolute purity. For example, the purity can be about 50% or more, about 60% or more, about 70% or more, about 80% or more, about 90% or more, or about 100%. The purity preferably is about 90% or more (e.g., about 90% to about 95%) and more preferably about 98% or more (e.g., about 98% to about 99%).

The inventive proteins, chimeric molecules (including functional portions and functional variants), nucleic acids, recombinant expression vectors, host cells, and populations of cells, all of which are collectively referred to as "inventive CdtB materials" hereinafter, can be formulated into a composition, such as a pharmaceutical composition. In this regard, the invention provides a pharmaceutical composition comprising any of the proteins, chimeric molecules (including functional portions and functional variants), nucleic acids, recombinant expression vectors, host cells, and populations of cells described herein, and a pharmaceutically acceptable carrier. The inventive pharmaceutical composition containing any of the inventive CdtB materials can comprise more than one inventive CdtB material, e.g., a polypeptide and a nucleic acid, or two or more different proteins. Alternatively, the pharmaceutical composition can comprise an inventive CdtB material in combination with one or more other pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CdtB material, as well as by the particular method used to administer the inventive CdtB material. Accordingly, there are a variety of suitable formulations of the pharmaceutical composition of the invention. The following formulations for parenteral (e.g., subcutaneous, intravenous, intraarterial, intramuscular, intradermal, interperitoneal, and intrathecal) and oral administration are exemplary and are in no way limiting. More than one route can be used to administer the inventive CdtB materials, and in certain instances, a particular route can provide a more immediate and more effective response than another route.

Formulations suitable for oral administration can include (a) liquid solutions, such as an effective amount of the inventive CdtB material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CdtB material in a flavor, usually sucrose and acacia or tragacanth, as well as pastilles comprising the inventive CdtB material in an inert base, such as gelatin and glycerin, or sucrose and acacia, emulsions, gels, and the like additionally containing such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive CdtB material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive CdtB material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. The requirements for effective pharmaceutical carriers for parenteral compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

It will be appreciated by one of skill in the art that, in addition to the above-described pharmaceutical compositions, the inventive CdtB materials of the invention can be formulated as inclusion complexes, such as cyclodextrin inclusion complexes, or liposomes.

For purposes of the invention, the amount or dose of the inventive CdtB material administered should be sufficient to effect a desired response, e.g., a therapeutic or prophylactic response, in the mammal over a reasonable time frame. For example, the dose of the inventive CdtB material should be sufficient to inhibit growth of a target cell or treat or prevent cancer in a period of from about 2 hours or longer, e.g., 12 to 24 or more hours, from the time of administration. In certain embodiments, the time period could be even longer. The dose will be determined by the efficacy of the particular inventive CdtB material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of symptoms), $LD_{50}$ (the dose lethal to 50% of the population), the $ED_{50}$ (the dose therapeutically effective in 50% of the population), and the therapeutic index in cell culture, animal studies, or combinations thereof. The therapeutic index is the ratio of $LD_{50}$ to $ED_{50}$ (i.e., $LD_{50}/ED_{50}$).

The dose of the inventive CdtB material also may be determined by the existence, nature, and extent of any adverse side effects that might accompany the administration of a particular inventive CdtB material. Typically, the attending physician will decide the dosage of the inventive CdtB material with which to treat each individual patient, taking into consideration a variety of factors, such as age, body weight, general health, diet, sex, inventive CdtB material to be administered, route of administration, and the severity of the condition being treated. By way of example and not intending to limit the invention, the dose of the inventive CdtB material can be about 0.001 to about 1000 mg/kg body weight of the subject being treated/day, from about 0.01 to about 10 mg/kg body weight/day, about 0.01 mg to about 1 mg/kg body weight/day, from about 1 to about to about 1000 mg/kg body weight/day, from about 5 to about 500 mg/kg body weight/day, from about 10 to about 250 mg/kg body weight/day, about 25 to about 150 mg/kg body weight/day, about 10 mg/kg body weight/day, about 2 mg/kg body weight/day to about 5 mg/kg body weight/day, or about 4 mg/kg body weight/day.

Alternatively, the inventive CdtB materials can be modified into a depot form, such that the manner in which the inventive CdtB material is released into the body to which it is administered is controlled with respect to time and location within the body (see, for example, U.S. Pat. No. 4,450,150). Depot forms of inventive CdtB materials can be, for example, an implantable composition comprising the inventive CdtB materials and a porous or non-porous material, such as a polymer, wherein the inventive CdtB materials is encapsulated by or diffused throughout the material, degradation of the non-porous material, or combinations thereof. The depot is then implanted into the desired location within the body and the inventive CdtB materials are released from the implant at a predetermined rate.

The inventive CdtB materials may be assayed for cytotoxicity by assays known in the art. Examples of cytotoxicity assays include a WST assay, which measures cell proliferation using the tetrazolium salt WST-1 (reagents and kits available from Roche Applied Sciences), as described in International Patent Application Publication WO 2011/032022.

In an embodiment of the invention, the pharmaceutical composition further comprises one or more PAs. The PA may be any suitable PA and may be as described herein with respect to other aspects of the invention. In an embodiment of the invention, the one or more PAs comprise any one or more of wtPA, PA-L1, PA-U2, PA-U7, PA-D512K, PA-GN, PA-NS, PA-R200A, and PA-I210A. The PA may or may not be conjugated or fused to a targeting moiety. The targeting moiety may be as described herein with respect to other aspects of the invention. The PA may be conjugated or fused to the targeting moiety either directly or indirectly through a linker, as described herein with respect to other aspects of the invention. Accordingly, a single pharmaceutical composition may comprise one or more of the inventive CdtB materials in combination with one or more PAs.

It is contemplated that the inventive pharmaceutical compositions, proteins, chimeric molecules, nucleic acids, recombinant expression vectors, host cells, or populations of cells can be used in methods of treating or preventing a condition such as, for example, cancer or human immunodeficiency virus (HIV). Without being bound by a particular theory or mechanism, it is believed that the inventive proteins destroy or inhibit the growth of cells through the degradation of nuclear DNA in host cells, inducing G2/M phase cell cycle arrest, inducing apoptosis, by reducing intracellular levels of plasma membrane-associated signal molecule phosphatidylinositol-3,4,5-triphosphate (PIP3), or combinations thereof. Without being bound to a particular theory or mechanism, it is believed that the inventive chimeric molecules including a targeting moiety recognize and specifically bind to cell surface markers, thereby delivering the cytotoxic protein to the population of cells expressing the cell surface marker with minimal or no cross-reactivity with cells that do not express the cell surface marker. In this way, the cytotoxicity of the proteins can be targeted to destroy or inhibit the growth of a particular population of cells, e.g., cancer cells. In this regard, the invention provides a method of treating or preventing a condition in a mammal comprising administering to the mammal any of the proteins, chimeric molecules, nucleic acids, recombinant expression vectors, host cell, population of cells, or pharmaceutical compositions described herein, in an amount effective to treat or prevent the condition in the mammal. In an embodiment, the condition is cancer or HIV. Preferably, the condition is cancer.

In an embodiment of the invention, the method further comprises administering one or more PAs to the mammal. The PA may be any suitable PA and may be as described herein with respect to other aspects of the invention. In an embodiment of the invention, the one or more PAs comprise any one or more of wtPA, PA-L1, PA-U2, PA-U7, PA-D512K, PA-GN, PA-NS, PA-R200A, and PA-I210A. The PA may or may not be conjugated or fused to a targeting moiety. The targeting moiety may be as described herein with respect to other aspects of the invention. The PA may be conjugated or fused to the targeting moiety either directly or indirectly through a linker, as described herein with respect to other aspects of the invention.

The method may comprise administering the inventive CdtB material and the PA simultaneously or sequentially to the mammal. In an embodiment of the invention, the method comprises administering the PA to the mammal prior to administering the inventive CdtB material or administering the inventive CdtB material after administering the PA to the mammal. In another embodiment, the method comprises administering the inventive CdtB material to the mammal prior to administering the PA or administering the PA after administering the inventive CdtB material to the mammal. Preferably, the method comprises administering the inventive CdtB material and the PA simultaneously to the mammal, e.g., in a single pharmaceutical composition.

In an embodiment, the method further comprises administering one or more immunosuppressive agents to the mammal in an amount effective to decrease the immune response to the inventive CdtB material. Administering one or more immunosuppressive agents to the mammal may, advantageously, eliminate or reduce an anti-CdtB material immune response including, for example, the production of anti-CdtB material antibodies and/or T-cells, that may otherwise undesirably neutralize the cytotoxic activity of the inventive CdtB material. In this regard, administering one or more immunosuppressive agents to the mammal may, advantageously, increase the amount of inventive CdtB material that can be given to the mammal which may, in turn, increase the effectiveness of the inventive CdtB material for treating a condition, such as, for example, cancer.

The method may comprise administering the inventive CdtB material and the one or more immunosuppressive agents simultaneously or sequentially to the mammal. While the method may comprise administering the one or more immunosuppressive agents to the mammal after administering the inventive CdtB material or simultaneously with the inventive CdtB material, preferably the method comprises administering the one or more immunosuppressive agents to the mammal prior to administering the inventive CdtB material. Administering the one or more immunosuppressive agents to the mammal prior to administering the inventive CdtB material advantageously may eliminate or reduce an undesirable immune response to the inventive CdtB material before the immune system is exposed to the inventive CdtB material. For example, the method may comprise administering the one or more immunosuppressive agents to the mammal about one to about seven days prior to administering the inventive CdtB material to the mammal.

The one or more immunosuppressive agents may comprise any agent suitable for suppressing an immune response to the inventive CdtB material. In an embodiment, the one or more immunosuppressive agents are selected from the group consisting of pentostatin, cyclophosphamide, and tofacitinib (Hassan et al., *Sci. Transl. Med.,* 5(208):208ra147 (2013); Mossoba et al., *Clin. Cancer Res.,* 17: 3697-3705 (2011); and Onda et al., *J. Immunol.,* 1400063; published ahead of print Jun. 2, 2014). In an embodiment of the invention, the one or more immunosuppressive agents comprise a combination of pentostatin and cyclophosphamide.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

With respect to the inventive methods, the cancer can be any cancer, including any of adrenal gland cancer, sarcomas (e.g., synovial sarcoma, osteogenic sarcoma, leiomyosarcoma uteri, angiosarcoma, fibrosarcoma, rhabdomyosarcoma, liposarcoma, myxoma, rhabdomyoma, fibroma, lipoma, and teratoma), lymphomas (e.g., small lymphocytic lymphoma, Hodgkin lymphoma, and non-Hodgkin lymphoma), hepatocellular carcinoma, glioma, head cancers (e.g., squamous cell carcinoma), neck cancers (e.g., squamous cell carcinoma), acute lymphocytic cancer, leukemias (e.g., hairy cell leukemia, myeloid leukemia (acute and chronic), lymphatic leukemia (acute and chronic), prolymphocytic leukemia (PLL), myelomonocytic leukemia (acute and chronic), and lymphocytic leukemia (acute and chronic)), bone cancer (osteogenic sarcoma, fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxoid fibroma, osteoid osteoma, and giant cell tumors), brain cancer (astrocytoma, medulloblastoma, glioma, ependymoma, geaninoma (pinealoma), glioblastoma multiforme, oligodendroglioma, schwannoma, and retinoblastoma), fallopian tube cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva (e.g., squamous cell carcinoma, intraepithelial carcinoma, adenocarcinoma, and fibrosarcoma), myeloproliferative disorders (e.g., chronic myeloid cancer), colon cancers (e.g., colon carcinoma), esophageal cancer (e.g., squamous cell carcinoma, adenocarcinoma, leiomyosarcoma, and lymphoma), cervical cancer (cervical carcinoma and pre-invasive cervical dysplasia), gastric cancer, gastrointestinal carcinoid tumor, hypopharynx cancer, larynx cancer, liver cancers (e.g., hepatocellular carcinoma, cholangiocarcinoma, hepatoblastoma, angiosarcoma, hepatocellular adenoma, and hemangioma), lung cancers (e.g., bronchogenic carcinoma (squamous cell, undifferentiated small cell, undifferentiated large cell, and adenocarcinoma), alveolar (bronchiolar) carcinoma, bronchial adenoma, chondromatous hamartoma, small cell lung cancer, non-small cell lung cancer, and lung adenocarcinoma), malignant mesothelioma, skin cancer (e.g., melanoma, basal cell carcinoma, squamous cell carcinoma, Kaposi's sarcoma, nevi, dysplastic nevi, lipoma, angioma, dermatofibroma, and keloids), multiple myeloma, nasopharynx cancer, ovarian cancer (e.g., ovarian carcinoma (serous cystadenocarcinoma, mucinous cystadenocarcinoma, endometrioid carcinoma, and clear cell adenocarcinoma), granulosa-theca cell tumors, Sertoli-Leydig cell tumors, dysgerminoma, and malignant teratoma), pancreatic cancer (e.g., ductal adenocarcinoma, insulinoma, glucagonoma, gastrinoma, carcinoid tumors, and VIPoma), peritoneum, omentum, mesentery cancer, pharynx cancer, prostate cancer (e.g., adenocarcinoma and sarcoma), rectal cancer, kidney cancer (e.g., adenocarcinoma, Wilms tumor (nephroblastoma), and renal cell carcinoma), small intestine cancer (adenocarcinoma, lymphoma, carcinoid tumors, Kaposi's sarcoma, leiomyoma, hemangioma, lipoma, neurofibroma, and fibroma), soft tissue cancer, stomach cancer (e.g., carcinoma, lymphoma, and leiomyosarcoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), cancer of the uterus (e.g., endometrial carcinoma), thyroid cancer, and urothelial cancers (e.g., squamous cell carcinoma, transitional cell carcinoma, adenocarcinoma, ureter cancer, and urinary bladder cancer). In an embodiment, the cancer is a tumor. The tumor may be, for example, a solid tumor or a liquid tumor.

As used herein, the tell "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Also provided is a method of inhibiting the growth of a target cell comprising contacting the cell with any of the proteins, chimeric molecules, nucleic acids, recombinant expression vectors, host cell, population of cells, or pharmaceutical compositions described herein, in an amount effective to inhibit growth of the target cell. The growth of the target cell may be inhibited by any amount, e.g., by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100%. The target cell may be provided in a biological sample. A biological sample may be obtained from a mammal in any suitable manner and from any suitable source. The biological sample may, for example, be obtained by a blood draw, leukapheresis, tumor biopsy necropsy, or combinations thereof. The contacting step can take place in vitro or in vivo with respect to the mammal. Preferably, the contacting is in vitro.

In an embodiment of the invention, the target cell is a cancer cell or an HIV-infected cell. Preferably, the target cell is a cancer cell. The target cell may be a cancer cell of any of the cancers described herein. In an embodiment of the invention, the target may express a cell surface marker. The cell surface marker may be any cell surface marker described herein with respect to other aspects of the invention.

In an embodiment of the invention, the method further comprises contacting the cell with one or more PAs. The PA may be any suitable PA and may be as described herein with respect to other aspects of the invention. In an embodiment of the invention, the one or more PAs comprise any one or more of wtPA, PA-L1, PA-U2, PA-U7, PA-D512K, PA-GN, PA-NS, PA-R200A, and PA-I210A. The PA may or may not be conjugated or fused to a targeting moiety. The targeting moiety may be as described herein with respect to other aspects of the invention. The PA may be conjugated or fused to the targeting moiety either directly or indirectly through a linker, as described herein with respect to other aspects of the invention.

The method may comprise contacting the cell with the inventive CdtB material and the PA simultaneously or sequentially. In an embodiment of the invention, the method comprises contacting the cell with the PA prior to contacting the cell with the inventive CdtB material or contacting the cell with the inventive CdtB material after contacting the cell with the PA. In another embodiment, the method comprises contacting the cell with the inventive CdtB material prior to administering the PA or contacting the cell with the PA after contacting the cell with the inventive CdtB material. Preferably, the method comprises contacting the cell with the inventive CdtB material and the PA simultaneously.

The following examples further illustrate the invention but, of course, should not be construed as in any way limiting its scope.

Example 1

This example demonstrates a method of producing a protein comprising CdtB conjugated or fused to *Bacillus anthracis* toxin lethal factor LFn (LFnCdtB).

LFnCdtB (SEQ ID NO: 3) includes the N-terminal 255 residues of anthrax toxin lethal factor (SEQ ID NO: 2) (LFn) fused to the N-terminus of an 11-residue peptide linker (SEQ ID NO: 4), which is, in turn, fused to the N-terminus of the 261 residues of CdtB (SEQ ID NO: 1).

The cDNA CdtB from *H. ducreyi* was amplified by PCR to generate the suitable restriction sites MluI and XmaI for cloning CdtB into the expression plasmid FP59AGGpYS for *B. anthracis* expression. The following signal sequence (from *B. anthracis* protective antigen): MKKRKVLIPL-MALSTILVSSTGNLEVIQ (SEQ ID NO: 5) (encoded by SEQ ID NO: 6) was generated.

LFnCdtB was expressed and purified generally as described in Park et al., *Protein Expression and Purification*, 18: 293-302 (2000). Expression was carried out in the plasmid-cured and non-infectious, protease-deficient *B. anthracis* strain BH460 (Pomerantsev et al., *Protein Expression and Purification*, 80: 80-90 (2011)). Following anion exchange chromatography, cation exchange chromatography was used as the final purification step. After elution from phenyl sepharose medium, samples were pooled and dialyzed against 20 mM Tris, pH 8, 0.5 mM EDTA overnight. The samples were loaded on a Q-SEPHAROSE FAST FLOW column (GE Healthcare, Waukesha, Wis.) for purification with an ÄKTA chromatography system (GE Healthcare, Waukesha, Wis.) and eluted using a linear gradient of 20 mM Tris, pH 8, 0.5 mM EDTA, 0.5 M NaCl. Fractions containing LFnCdtB were dialyzed against 20 mM citric acid, pH 6.8, 0.5 mM EDTA overnight and loaded on an S-SEPHAROSE FAST FLOW column (GE Healthcare, Waukesha, Wis.) for purification with an ÄKTA chromatography system and eluted using a linear gradient of 20 mM citric acid, pH 6.8, 0.5 mM EDTA, 0.5 M NaCl. Fractions containing LFnCdtB were dialyzed against 5 mM HEPES, pH 7.2, 0.5 mM EDTA, concentrated (Amicon Ultrafiltration devices, 30 kDa molecular weight cutoff, Millipore, Billerica, Mass.), filter sterilized, and stored in aliquots at −80° C. With a culture volume of 5 L, a total yield of 17 mg or 3.4 mg LFnCdtB/mL culture medium was achieved. Purified LFnCdtB was analyzed by electrospray ionization mass spectrometry to confirm that the mass matched the mass calculated from the sequence.

The results showed that LFnCdtB was successfully purified from a non-virulent plasmid-cured and protease deficient *B. anthracis* strain. The protein was secreted to the supernatant and purified in yields of at least 0.8 mg per liter of culture with a very high purity.

Example 2

This example demonstrates the enzymatic activity of LFnCdtB.

The enzymatic activity of LFnCdtB was confirmed and compared to that of CdtB in a DNA cleavage assay (DNase Activity Assay). Plasmid DNA (1 μg) was incubated with 25 pmol of CdtB or LFnCdtB or 1 μL DNase I at 37° C. for 2 hours (h) in a total volume of 15 μL 25 mM HEPES, pH 7.2, 50 mM $MgCl_2$. The samples were analyzed on a 0.7% agarose gel.

The results showed that the enzymatic activity of LFnCdtB was similar to that of CdtB.

Example 3

This example demonstrates the cytotoxic activity of LFnCdtB.

Cell culture experiments were performed on HeLa cells (human cervical carcinoma cell line), WTP4 CHO K1 cells (Chinese hamster ovary cells), HN6 cells (human head and neck cancer cell line), RAW264.7 cells (murine leukemic monocyte/macrophages), LL3 cells (murine Lewis Lung carcinoma cells), B16/BL6 (murine melanoma cells), and T241 (murine fibrosarcoma cells). Additional human cell lines of the NCI-60 panel used for experiments include: melanoma cells (C32, Malme-3M, SK-MEL-2, SK-MEL-24, SK-MEL-28), colon carcinoma cells (COLO 205, HCC2998, SW620), lung carcinoma (A549 and NCI-H226), renal carcinoma (A-498 and SC12C), and breast carcinoma (MDA-MB-231 and Hs 578T).

WTP4 CHO K1 cells were maintained in modified Eagle's medium alpha with GLUTAMAX-1 medium (Gibco, Life Technologies, Grand Island, N.Y.). All other cells were maintained in Dulbecco's modified Eagle's medium with GLUTAMAX-1 medium (Gibco, Life Technologies, Grand Island, N.Y.). All media were supplemented with 20% (LL3 and B16/BL6 cells) or 10% (all other cells) fetal bovine serum (Gibco, Life Technologies, Grand Island, N.Y.) and 50 μg/mL gentamicin (Quality Biological, Gaithersburg, Md.).

A fusion protein, including LFn and the catalytic domain of *Pseudomonas exotoxin* A (FP59AGG, similar to FP59 described in Park et al., *Protein Expression and Purification*, 18: 293-302 (2000) but with the wildtype AGG N-terminus of LF) was prepared and purified. FP59AGG was used as a control for effective cell killing. FP59AGG, wildtype protective antigen (PA), and tumor-specific PA-L1 were expressed and purified generally as described in Liu et al., *Cell. Microbiol.*, 9:977-87 (2007).

Dose-response curves for the combination of PA+LFn fusion proteins (LFnCdtB and FP59AGG) or CdtB were obtained by incubation on cells for 72 h. The cells (5,000 cells per well in 100 μL medium) were seeded in 96-well plates and incubated at 37° C. overnight before addition of PA and the LFn fusion proteins. PA and LFn fusion proteins were added in 100 μL, medium (modified Eagle's medium alpha with GLUTAMAX-1 medium or Dulbecco's modified Eagle's medium with GLUTAMAX-1 medium) to achieve final concentrations of 250 ng/mL of PA (both wildtype (wt) PA and PA-L1) and 10 nM-100 nM of LFn fusion proteins or CdtB, depending on the tested cell lines. The cells were incubated an additional 72 h, and cell survival was determined in an 3-(4,5-Dimethylthiazol-2-yl)-2,5-diphenyltetrazolium bromide (MTT, Sigma Aldrich, St. Louis, Mo.) assay.

As shown in FIGS. 1A-1D, the 72-h exposure to 250 ng/mL PA+LFnCdtB in varying concentrations resulted in dose-dependent cytotoxicity. The degree of cytotoxicity observed for the various cells was in the order: CHO K1>RAW=HeLa>HN6. No relevant cytotoxicities were observed at concentrations of up to 100 nM CdtB for cells that were incubated with 250 ng/mL PA+CdtB.

The 50% survival index ($SI_{50}$) values were calculated. The 50% survival indices ($SI_{50}$, 50% cell survival in comparison to untreated controls) values for cytotoxicity analyses were obtained from a nonlinear regression curve fit using GraphPad PRISM 5.02. The method used for the nonlinear regression curve fit was "log(inhibitor) versus normalized response" (by using a least square fit). The results are shown in Table 1. As shown in Table 1, the observed $SI_{50}$ values were in the range of 0.5 pM (CHO K1) to 142 pM (HN6) for RAW264.7, HN6, HeLa, and WTP4 CHO K1 cells.

Figure 2:
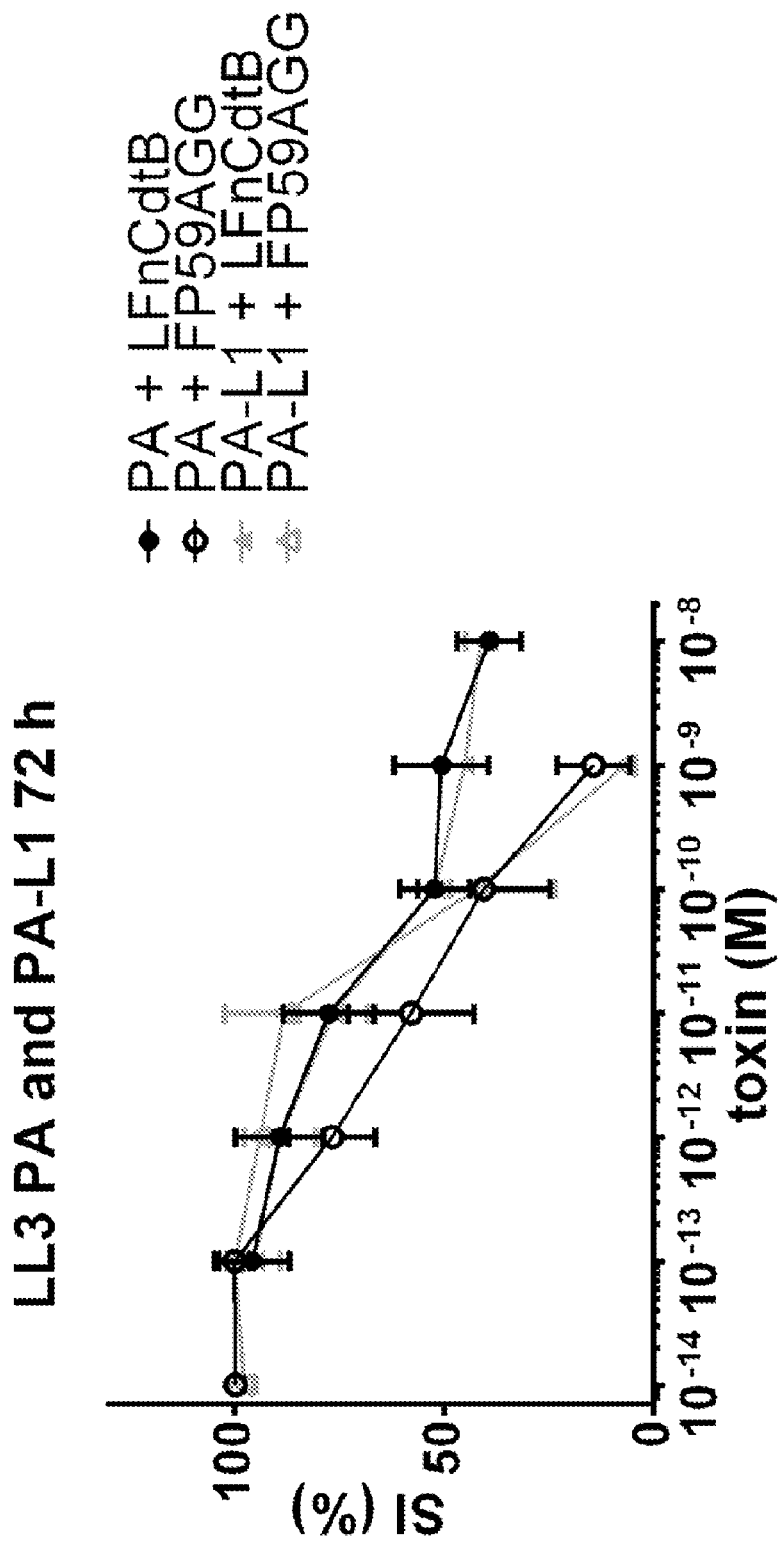
FIG. 2 is a graph showing SI (%) of LL3 cells treated with (a) PA and LFnCdtB (closed circles), (b) PA and FP59AGG (open circles), (c) PA-L1 and LFnCdtB (closed triangles), or (d) PA-L1 and FP59AGG (open triangles). The amount of LFnCdtB or FP59AGG varied as shown.

Murine LL3 cells were incubated with 250 ng/mL wild type PA or 250 ng/mL matrix metalloproteinase-2-activated PA-L1 in combination with LFnCdtB or FP59AGG at varying concentrations. The results are shown in FIG. 2 and Table 1. As shown in FIG. 2 and Table 1, incubation with PA and PA-L1 resulted in similar cytotoxicities for both LFn fusion proteins ($SI_{50}$ values for LFnCdtB were 0.76 and 0.33 nM, respectively, and $SI_{50}$ values for FP59AGG were 0.026 and 0.076 nM, respectively). FP59AGG was more cytotoxic, but the marginal differences between wild type PA and PA-L1 for both fusion proteins indicate successful activation of PA-L1.

Fourteen human tumor cell lines of the NCI-60 cell panel from the National Cancer Institute and two murine tumor cell lines (B16/BL6, a murine melanoma cell line and T241, a murine fibrosarcoma cell line) were also tested for cytotoxicity induced by PA+LFnCdtB or PA+FP59AGG under conditions the same as those described above. The results are summarized in Table 1. Several cell lines were highly sensitive to LFnCdtB with $SI_{50}$ values in the pM range.

TABLE 1

| | $SI_{50}$ (nM) | |
|---|---|---|
| Cell line | LFnCdtB | FP59AGG |
| Melanoma | | |
| C32 | 0.00035 | 0.0022 |
| Malme-3M | >>10 | 0.0027 |
| SK-MEL-2 | >>10 | 0.010 |
| SK-MEL-24 | 0.77 | 0.017 |
| SK-MEL-28 | >10 | 0.0021 |
| Colon | | |
| COLO 205 | 0.11 | 0.008 |
| HCC2998 | 0.085 | 0.0037 |
| SW620 | 0.31 | 0.024 |
| Lung | | |
| A549 | 1.6 | 0.002 |
| NCI-H226 | >10 | 0.00043 |
| Breast | | |
| MDA-MB-231 | 0.018 | 0.0068 |
| Hs 578T | 0.18 | 0.037 |

TABLE 1-continued

| Cell line | SI$_{50}$ (nM) | |
|---|---|---|
| | LFnCdtB | FP59AGG |
| Kidney | | |
| A-498 | 0.072 | 0.008 |
| SN12C | 0.083 | 0.00038 |
| HN6 (head and neck) | 0.14 | ND |
| HeLa (cervical) | 0.0037 | ND |
| Murine/Chinese hamster | | |
| CHO K1 (Chinese hamster) | 0.00048 | ND |
| RAW264.7 | 0.0037 | ND |
| T241 | 0.27 | 0.064 |
| LL3 (PA) | 0.76 | 0.026 |
| LL3 (PA-L1) | 0.33 | 0.073 |
| B16/BL6 (PA) | 0.021 | 0.0005 |
| B16/BL6 (PA-L1) | 0.038 | 0.054 |

ND = not determined nologies, Grand Island, N.Y.) according to the manufacturer's instructions. Cellular fluorescence was determined by flow cytometry on an LSR II flow cytometer (BD Biosciences, San Jose, Calif.) using the green fluorescent protein (GFP) channel and counting 10,000 cells. Analyses of cell cycle arrest and TUNEL-positive cells were performed by using FLOWJO. The percentage of cells in the G0/G1 phase and in the G2/M phase was analyzed by using the cell cycle analysis of FLOWJO.

The results of the propidium iodide staining are shown in Table 2 and demonstrate that treatment with PA+LFnCdtB induces a potent cell cycle arrest in G2/M phase. Staurosporine was used as a control for apoptosis induction without affecting the cell cycle. A strong increase in the population of cells in G2/M phase was detected after 8 h of toxin exposure. Nearly all cells were arrested in G2/M after 14 h, at which point more apoptotic cells with very low PI intensity were detected. Cells treated with PA+FP59AGG showed no cell cycle arrest after 24 or 48 h but a high number of apoptotic cells was detected after 48 h. Table 2 shows the percentage of cells in the G0/G1 phase and in the G2/M phase at various time points.

TABLE 2

| | 4 h | | 8 h | | 14 h | | 24 h | | 48 h | |
|---|---|---|---|---|---|---|---|---|---|---|
| | % G0/G1 | % G2/M | % G0/G1 | % G2/M | % G0/G1 | % G2/M | % G0/G1 | % G2/M | % G0/G1 | % G2/M |
| CdtB | 50.4 | 15.3 | 46.1 | 23.6 | 48.6 | 17.2 | 54.8 | 18.8 | 55.4 | 14.2 |
| FP59AGG | 47.6 | 17.5 | 46.2 | 19.3 | 53.1 | 13.9 | 47.3 | 16.7 | 27.5 | 12.8 |
| LFnCdtB | 39.4 | 21.3 | 23.3 | 38.7 | 7.0 | 63.9 | 4.3 | 73.0 | 0 | 56.2 |
| Staurosporine | 42.9 | 13.6 | 41.8 | 12.2 | — | — | — | — | — | — |
| Mock | 51.4 | 13.9 | — | — | — | — | — | — | — | — |

Mock-treated cells (Mock) were treated with wildtype PA only and analyzed after 4 h incubation.

Example 4

This example demonstrates the ability of LFnCdtB to arrest the cell cycle and to induce apoptosis of target cells.

CHO K1 cells were used to study the effect of LFnCdtB on the cell cycle of toxin-exposed cells. CHO K1 cells (WTP4) (0.2×10$^6$ cells per well overnight in 6 well-plates) were incubated with 250 ng/mL PA and 100 pM CdtB or LFnCdtB or 0.1 pM FP59AGG in 800 µL cell culture medium for 1-48 h. Cells were further incubated with 1 µM staurosporine as a positive control for the terminal deoxynucleotidyl transferase dUTP nick end labeling (TUNEL) assay. Cells were released using trypsin and resuspended in 1 mL cell culture medium, centrifuged (5 min, 200×g, 4° C.), and resuspended in 1 mL PBS. Cold 100% ethyl alcohol (2.5 mL) was added one drop at a time under constant mixing to fix the cells, and the cells were incubated either 15 minutes (min) on ice or overnight at −20° C. For cell cycle analysis by propidium iodide staining, cells were centrifuged (5 min, 430×g, 4° C.), and resuspended in 500 µL staining solution (50 µg/mL propidium iodide (Life Technologies, Grand Island, N.Y.), 0.1 mg/mL RNase A (Qiagen, Valencia, Calif.), 0.05% Triton X-100). The cells were incubated for 40 min at 37° C. and 3 mL PBS was added. The cells were centrifuged for 5 min (430×g, 4° C.), after which 3 mL supernatant was removed, and cellular fluorescence was measured by flow cytometry on an LSR II flow cytometer (BD Biosciences, San Jose, Calif.) using the TEXAS RED channel and counting 25,000 cells. Detection of DNA damage with the TUNEL assay was performed on cells treated and fixed as described above. TUNEL staining was performed with the APO-BrdU TUNEL Assay Kit (Life Tech- Apoptosis induction by LFnCdtB was analyzed by poly-ADP-ribose-polymerase (PARP) cleavage on HeLa cells and by terminal deoxynucleotidyl transferase dUTP nick end labeling (TUNEL) staining on CHO K1 cells. Anti-poly-ADP-ribose-polymerase (PARP) polyclonal antibodies (BD Biosciences, San Jose, Calif.) were used for PARP cleavage. All primary antibodies were detected using infrared dye-conjugated secondary antibodies on the ODYSSEY Imager infrared detection system (LI-COR, Lincoln, Nebr.). For apoptosis detection, HeLa cells (1×10$^6$ cells per well overnight in 6-well plates) were incubated with 250 ng/mL PA and 10 nM LFnCdtB or CdtB in 800 µL medium for 24-72 h. In addition, cells were incubated with 1 µM staurosporine for 2 h. Cells were washed and scraped off in 100 µl PBS+1% Triton X-100, incubated 30 min at 4° C. on a rotary shaker, and centrifuged (30 min, 16,000×g, 4° C.). Supernatants were incubated a further 7 h at 37° C., and total protein concentration was determined by BCA assay (Thermo Fisher Scientific, Rockford, Ill.). Total protein (100 µg) was separated by SDS PAGE and Western blotted using the IBLOT system (Invitrogen, Life Technologies, Grand Island, N.Y.).

The PARP cleavage detection showed apoptosis induction by the positive control staurosporine after 2 h exposure on the cells. PA+CdtB failed to induce apoptosis in HeLa cells and only a low amount of cleaved PARP was detected after 48 and 72 h, most likely due to dying cells in the crowded culture dish. PA+LFnCdtB induced a strong apoptotic signal after 48 and 72 h. The amount of detectable actin in the LFnCdtB-treated samples was very low. This could indicate effects of prolonged apoptosis in these cells.

For the TUNEL assay, cells were fixed with ethanol, stained by TUNEL staining to quantify apoptotic cells, and 10,000 cells were counted by flow cytometry. TUNEL-positive apoptotic cells were gated by high fluorescence and the percentage is indicated in Table 3. The TUNEL assay showed slightly increased numbers of apoptotic cells after PA+LFnCdtB treatment in CHO K1 cells after 14 and 24 h (Table 3). After 48 h of toxin exposure, more than 90% of detected cells were positive for TUNEL staining. Additional cells were treated with PA+FP59AGG and the result was similar as that obtained for PA+LFnCdtB. The number of apoptotic cells after 24 h appeared to be higher as a consequence of PA+FP59AGG treatment. Staurosporine induced a very strong increase in apoptotic cells after 4 h (50% of cells positive for TUNEL staining) and a complete conversion of cells (>TUNEL positive) after 8 h while PA+CdtB failed to induce apoptosis.

TABLE 3

| | % TUNEL positive cells | | | | |
|---|---|---|---|---|---|
| | 4 h | 8 h | 14 h | 24 h | 48 h |
| CdtB | 0.620 | 0.510 | 0.89 | 0.25 | 0.13 |
| FP59AGG | 0.560 | 0.670 | 3.79 | 18.1 | 90.6 |
| LFnCdtB | 0.800 | 0.712 | 6.26 | 4.77 | 84.1 |
| Staurosporine | 33.9 | 90.0 | — | — | — |
| Mock | 0.650 | — | — | — | — |

Mock-treated cells (Mock) were treated with wildtype PA only and analyzed after 4 h incubation.

Example 5

This example demonstrates the intracellular localization and nuclear action of LFnCdtB.

LFnCdtB was biotinylated for intracellular detection to improve the sensitivity of the detection system. For the intracellular detection, CHO K1 (WTP4) cells ($1.75 \times 10^6$ cells per well overnight in 6-well plates) were incubated with 250 ng/mL PA and 5 nM LFnCdtB or FP59AGG in 800 µL medium for 1 or 4 h. In addition, cells were incubated for 4 h with 100 nM CdtA, CdtB, and CdtC each (Cdt). LFnCdtB was biotinylated prior to addition to cells using (+)-Biotin N-hydroxysuccinimide ester (Sigma, St. Louis, Mo.). After the indicated incubation time, cytosolic fractions and nuclear fractions were isolated using the "Nuclear Extract Kit" (Active Motif, Carlsbad, Calif.) according to the manufacturer's instructions. Total protein concentrations were determined using the PROSTAIN assay (Active Motif, Carlsbad, Calif.). Total protein (40 µg) was separated by SDS PAGE and Western blotted using the IBLOT system (Invitrogen, Life Technologies, Grand Island, N.Y.) and the Western Blot Signal Enhancer kit (Thermo, Waltham, Mass.) for signal enhancement. For intracellular localization, cytosolic marker protein MEK2 and nuclear marker protein p84 were detected by antibodies (anti-MEK2 (N-20), rabbit polyclonal IgG sc-524, Santa Cruz, Dallas, Tex.; anti-p84, monoclonal rabbit IgG ab131268, abeam, Cambridge, Mass.). Detection of LFn-, CdtB-, and PEIII-containing proteins was achieved with sera from rabbit (anti-LF), mouse (anti-CdtB) and goat (anti-PE, List Biological Laboratories, Campbell, Calif.).

LFnCdtB was detected both in cytosolic and nuclear fractions of CHO K1 cells after 1 and 4 h fusion protein exposure by Western blotting. The use of p84 and MEK2 as marker proteins for the nucleus (p84) and the cytosol (MEK2) showed that no contaminations of fractions occurred. Additional endogenous biotinylated carboxylase proteins were detected by streptavidin detection in the nuclear fraction (weak protein band above 95 kDa) and in the cytosolic fraction (protein bands at approximately 70, 75, and 125 kDa). A control treatment with wildtype Cdt resulted in the localization of CdtB mainly in the nuclear fraction. A further control treatment with PA+FP59AGG located FP59AGG in the nuclear and the cytosolic fraction.

Nuclear activity of LFnCdtB was detected by immunofluorescence detection of pH2A.X. HeLa cells ($0.2 \times 10^6$ cells per well overnight in 24-well plates on cover slips) were incubated with 250 ng/mL PA and 10 nM LFnCdtB or 10 nM FP59AGG or with 100 nM Cdt for 1-24 h. Cells were fixed and permeabilized by 4% paraformaldehyde and 0.1% Triton X-100 in PBS for 15 min, and incubated with antibodies against phosphorylated histone H2A.X (pH2A.X, Cell Signaling, Danvers, Mass.) for 2 h after blocking with PBS+ 0.05% Tween 20+1% bovine serum albumin. Bound primary antibodies were detected by ALEXA-FLUOR 488-conjugated secondary antibodies and cellular DNA was stained by 4',6-diamidino-2-phenylindole (DAPI, 1 µg/mL in PBS). Images of mounted cover slips were taken by confocal laser scanning microscopy on a SP5 microscope (Leica, Buffalo Grove, Ill.).

HeLa cells treated with PA+LFnCdtB or treated with wildtype Cdt showed a clear increase in H2AX phosphorylation after 8 h. The signal was still increased after 24 h but appeared to get weaker especially for PA+LFnCdtB treatment, possibly a result of induced apoptosis. PA+FP59AGG resulted in a very weak increase of phosphorylation compared to PA+LFnCdtB treatment. This could also be a side effect of apoptosis induction in FP59AGG treated cells.

Example 6

This example demonstrates the treatment of LL3 tumors in mice using LFnCdtB.

LFnCdtB was administered with the matrix metalloproteinase-activated PA-L1 or with wildtype PA to mice having implanted LL3 mouse melanoma cell tumors. All animal experiments were performed under protocols approved by the NIAID Animal Care and Use Committee. Both male and female C57BL/6 mice (Jackson Labs, Bar Harbor, Me.) were injected with $0.8 \times 10^6$ LL3 mouse melanoma cells subcutaneously (s.c.) in the neck on day 0. After 5 days (all tumors with a width of a least 4 mm), mice were randomly assigned to three groups of ten or 13 mice each and injected with 200 µL sterile PBS with different drug combinations intraperitoneally (i.p.) every other day (days 5, 7, 9, 12, 14, 16). Mice were treated with PBS (13 mice), 100 µg wildtype PA+100 µg LFnCdtB in PBS (10 mice), or 100 µg PA-L1 (PA with a mutated furin cleavage site to achieve tumor-selective cleavage and activation of PA by matrix metalloproteinase-2 (10))+100 µg LFnCdtB in PBS (10 mice). Tumors and mouse body weight were measured every other day with a caliper and tumor mass calculated (tumor mass (mg)=(width (all in mm)×depth×height)/2) with a final measurement on day 19. Mice with tumors with one diameter exceeding 20 mm or ulceration or more than 20% body weight loss were euthanized. Relative body weight values and tumor weight was statistically compared by a paired t-test. A two-tailed significance of p≤0.05 was interpreted as being statistically significant.

Figure 3:
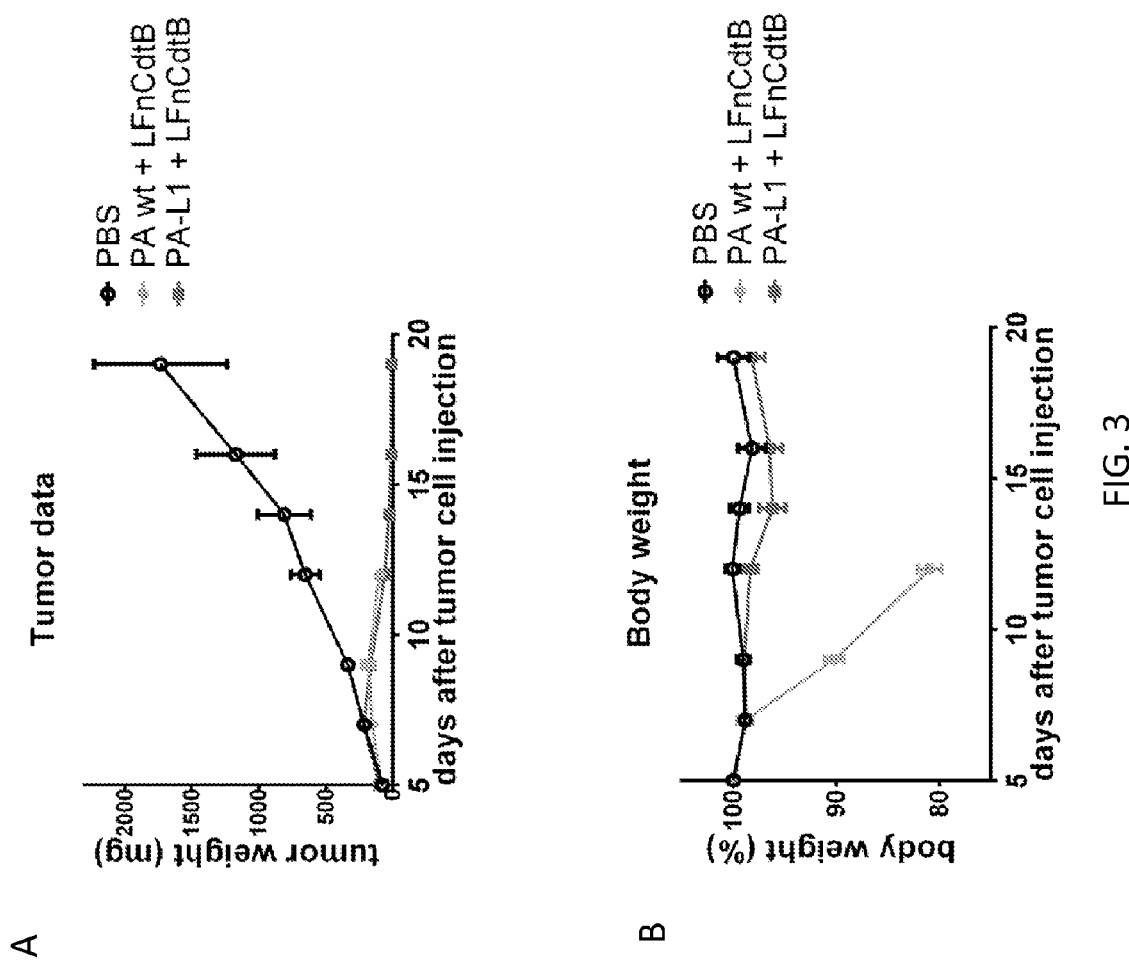
FIGS. 3A and 3B are graphs showing tumor weight (mg) (A) or body weight (%) (B) in LL3 tumor-bearing mice treated with phosphate buffered saline (PBS) (open circles), wildtype (wt) PA and LFnCdtB (closed circles), or PA-L1 and LFnCdtB (squares) measured at days after tumor cell injection.

Treatment with PA-L1+LFnCdtB resulted in no significant change in body weight, while PA+LFnCdtB resulted in nearly 20% body weight loss on day 12 (FIG. 3B) and two mice were found dead on day 12. The mice in this group were only injected three times with PA+LFnCdtB (days 5, 7, and 9) and euthanized on day 13 since no recovery in body weight was observed. PA-L1+LFnCdtB treatment resulted in strong tumor growth inhibition (FIG. 3A). PA+LFnCdtB treatment inhibited tumor growth as observed on day 12. Due to rapid tumor growth and ulceration in the PBS group, all mice were euthanized on day 19. One mouse treated with PA-L1+LFnCdtB died on day 23, seven days after the last injection with PA-L1+LFnCdtB. No side effects of the treatment were observed and the cause of death remained unclear. At this time, this mouse was tumor-free (by palpation). On day 19 (three days after the last injection) five of ten mice of the PA-L1+LFnCdtB group were tumor-free. Without further injection, eight out of nine surviving mice on day 28 were tumor-free and remained tumor-free for the next two months. The mouse with the remaining tumor was euthanized after two weeks due to the regrowing tumor. These results suggest that LFnCdtB treats tumors and has very low systemic toxicity.

Example 7

This example demonstrates the treatment of B16/BL6 tumors in mice using LFnCdtB. This example also demonstrates the treatment of tumors in mice using a lower dosage of LFnCdtB as compared to the dose employed in Example 6.

LFnCdtB was administered with the matrix metalloproteinase-activated PA-L1 to mice having implanted B16/BL6 mouse melanoma cell tumors. Mice were injected with melanoma cells as described in Example 6. Mice were treated with PBS (13 mice), 60 μg PA-L1+30 μg LFnCdtB in PBS (12 mice), 30 μg PA-L1+15 μg LFnCdtB in PBS (11 mice), or 60 μg PA-L1+15 μg LFnCdtB+15 μg LF (Lethal Factor original sequence (LFOS) (SEQ ID NO: 10)) in PBS (11 mice). Mice that lacked expression of CMG2, which is the receptor for PA, (CMG2−/−) were treated with 60 μg PA-L1+30 μg LFnCdtB in PBS (5 mice). Tumors and mouse body weight were measured every other day with a caliper and tumor mass calculated (tumor mass (mg)=(width (all in mm)×depth×height)/2) with a final measurement on day 19. Mice with tumors with one diameter exceeding 20 mm or ulceration or more than 20% body weight loss were euthanized.

Figure 4:
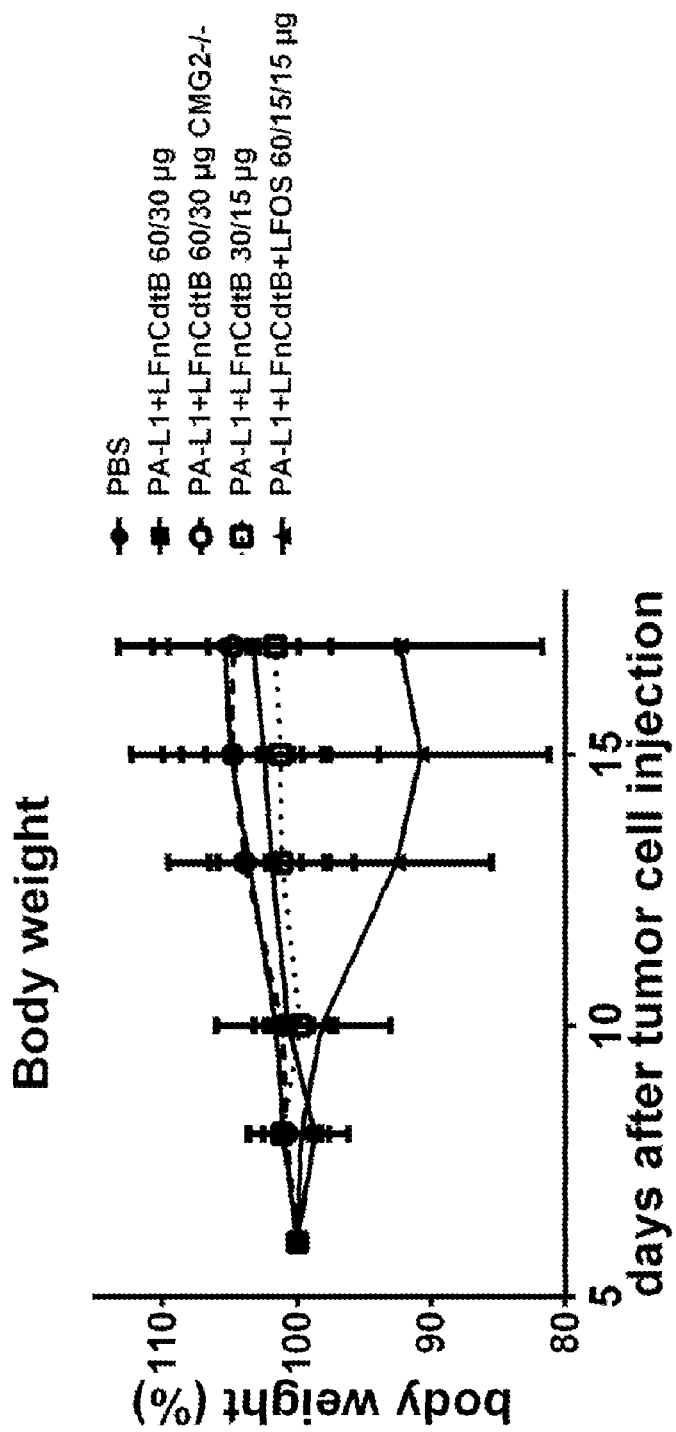
FIGS. 4 and 5 are graphs showing body weight (%) (FIG. 4) or tumor weight (mg) (FIG. 5) in B16/BL6 tumor-bearing mice treated with PBS (closed circles), 60 µg PA-L1+30 µg LFnCdtB in PBS (closed squares), 30 µg PA-L1+15 µg LFnCdtB in PBS (open squares), or 60 µg PA-L1+15 µg LFnCdtB+15 µg LF (LFOS) (triangles). Mice that lacked expression of CMG2 (CMG2−/−) were treated with 60 µg PA-L1+30 µg LFnCdtB in PBS (open circles).
Figure 5:
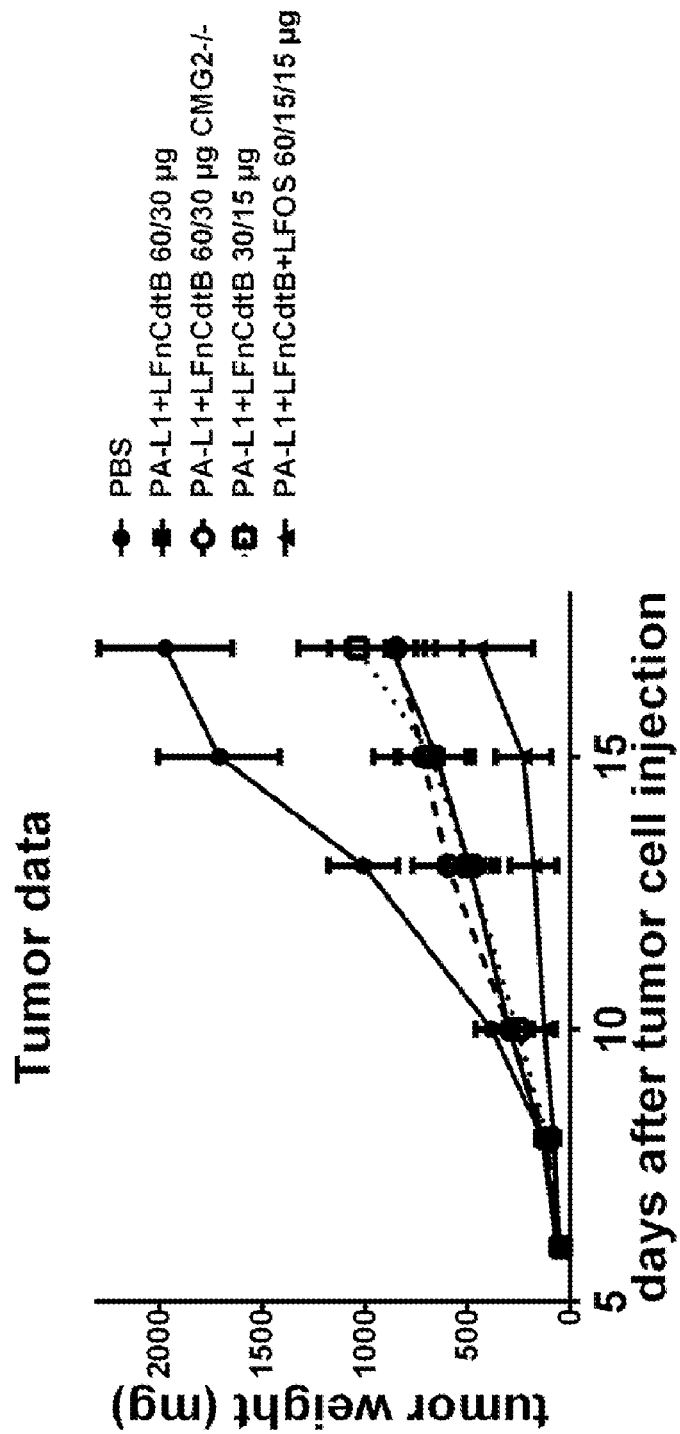

The results are shown in FIGS. 4 and 5. As shown in FIG. 4, treatment with PA-L1+LFnCdtB resulted in no significant change in body weight, while PA+LFnCdtB+LFOS resulted in body weight loss around day 12. As shown in FIG. 5, reduced tumor growth was observed in mice treated with a third of the LFnCdtB dose that was administered in Example 6. An increased reduction in tumor growth was observed in mice treated with the combination of PA, LFnCdtB, and LF. Without being bound by a particular theory or mechanism, it is believed that LF acts on the tumor vasculature and helps to eliminate nutritional support of the tumor. These results suggest that LFnCdtB treats tumors and has very low systemic toxicity, and that LFnCdtB may act directly on the B16/BL6 tumor cells.

Example 8

This example demonstrates the blood enzyme levels of LL3 tumor-bearing mice treated with LFnCdtB.

Blood enzyme levels were analyzed after 6 injections (days 5, 7, 9, 12, 14, 16) of (1) 100 μg PA-L1+100 μg LFnCdtB or (2) PBS into the peritoneum of tumor-bearing C57BL/6 mice of Example 6. Each group included 5 mice and for statistical analysis, data of 15 further mice treated similarly with PBS were applied. Blood was collected 1 h after the last injection, and the plasma was prepared to measure alanine aminotransferase, aspartate aminotransferase, lactate dehydrogenase, and creatine kinase. For statistical analysis of blood enzyme levels, data of 15 mice treated with PBS for other experiments were included and compared by using the unpaired t-test (GRAPHPAD Prism 5.02).

Analysis of blood enzymes showed no increase of alanine aminotransferase and lactate dehydrogenase and mild increases of aspartate aminotransferase (p=0.029) and creatine kinase (p=0.02) at the end of the treatment regimen with PA-L1 and LFnCdtB. These data support the previous observation of little or no side effects with the administration of LFnCdtB, and further demonstrate the suitability of LFnCdtB as an anti-tumor drug.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A protein comprising a cytolethal distending toxin subunit B (CdtB) conjugated or fused to a *Bacillus anthracis* toxin lethal factor (LF) or a functional portion of LF.

2. The protein of claim 1, wherein the CdtB is *Haemophilus ducreyi* CdtB.

3. The protein of claim 1, wherein the CdtB comprises SEQ ID NO: 1.

4. The protein of claim 1, wherein the LF or functional portion thereof comprises SEQ ID NO: 2.

5. The protein of claim 1, wherein the protein comprises SEQ ID NO: 3.

6. A chimeric molecule comprising (a) (i) a targeting moiety, (ii) a *Bacillus anthracis* protective antigen (PA), or (iii) both (i) and (ii) conjugated or fused to (b) the protein of claim 1.

7. The chimeric molecule according to claim 6, wherein the PA is wild-type PA (wtPA), PA-L1, PA-U2, PA-U7, PA-D512K, PA-GN, PA-NS, PA-R200A, or PA-I210A.

8. The chimeric molecule of claim 6, wherein the targeting moiety is a monoclonal antibody, antigen-binding portion of an antibody, peptide, hormone, growth factor, or cytokine.

9. The chimeric molecule of claim 8, wherein the targeting moiety is a monoclonal antibody or an antigen binding portion thereof.

10. The chimeric molecule of claim 9, wherein the monoclonal antibody or antigen binding portion thereof specifically binds to a cell surface marker selected from the group consisting of CD19, CD21, CD22, CD25, CD30, CD33, CD79b, CD123, epidermal growth factor receptor variant III (EGFRvIII), interleukin-15 receptor, interleukin-8 receptor, interleukin-2 receptor, transferrin receptor, epidermal growth factor (EGF) receptor, mesothelin, cadherin, Lewis Y, vascular endothelial growth factor (VEGF) receptor, HER2, estrogen receptor, carcinoembryonic antigen, prostate-specific membrane antigen, prostate-specific antigen, interleukin (IL)-13 receptor, IL-4 receptor, IL-3 receptor, granulocyte-macrophage colony-stimulating factor (GM-CSF) receptor, CD4, gp160, gp120, HIV-1 gag (p24), and gp41.

11. The chimeric molecule of claim 6, wherein the targeting moiety is an antibody selected from the group consisting of B3, RFB4, SS, HN1, HN2, and antigen binding portions thereof.

12. A nucleic acid comprising a nucleotide sequence encoding the protein of claim 1.

13. A pharmaceutical composition comprising (a) the protein of claim 1 and (b) a pharmaceutically acceptable carrier.

14. The pharmaceutical composition of claim 13, further comprising one or more PAs.

15. The pharmaceutical composition of claim 14, wherein the one or more PAs comprise any one or more of wtPA, PA-L1, PA-U2, PA-U7, PA-D512K, PA-GN, PA-NS, PA-R200A, and PA-I210A.

16. The pharmaceutical composition of claim 14, wherein the one or more PAs are conjugated or fused to a targeting moiety.

17. A method of producing the protein of claim 1, the method comprising (a) recombinantly expressing the protein and (b) purifying the protein.

18. A method of producing the chimeric molecule of claim 6 comprising (a) recombinantly expressing the chimeric molecule and (b) purifying the chimeric molecule.

19. A method of producing a chimeric molecule comprising (a) recombinantly expressing the protein of claim 1, (b) purifying the protein, and (c) covalently linking (i) a PA, (ii) a targeting moiety or (iii) both (i) and (ii) to the purified protein.

20. A method of inhibiting the growth of a target cell, the method comprising contacting the cell with the protein of claim 1 in an amount effective to inhibit growth of the target cell.

* * * * *

SEQUENCE LISTING

<160> NUMBER OF SEQ ID NOS: 17

<210> SEQ ID NO 1
<211> LENGTH: 261
<212> TYPE: PRT
<213> ORGANISM: Haemophilus ducreyi

<400> SEQUENCE: 1

Asn Leu Ser Asp Phe Lys Val Ala Thr Trp Asn Leu Gln Gly Ser Ser
1               5                   10                  15

Ala Val Asn Glu Ser Lys Trp Asn Ile Asn Val Arg Gln Leu Leu Ser
            20                  25                  30

Gly Glu Gln Gly Ala Asp Ile Leu Met Val Gln Glu Ala Gly Ser Leu
        35                  40                  45

Pro Ser Ser Ala Val Arg Thr Ser Arg Val Ile Gln His Gly Gly Thr
50                  55                  60

Pro Ile Glu Glu Tyr Thr Trp Asn Leu Gly Thr Arg Ser Arg Pro Asn
65                  70                  75                  80

Met Val Tyr Ile Tyr Tyr Ser Arg Leu Asp Val Gly Ala Asn Arg Val
                85                  90                  95

Asn Leu Ala Ile Val Ser Arg Arg Gln Ala Asp Glu Ala Phe Ile Val
            100                 105                 110

His Ser Asp Ser Ser Val Leu Gln Ser Arg Pro Ala Val Gly Ile Arg
        115                 120                 125

Ile Gly Thr Asp Val Phe Phe Thr Val His Ala Leu Ala Thr Gly Gly
    130                 135                 140

Ser Asp Ala Val Ser Leu Ile Arg Asn Ile Phe Thr Thr Phe Asn Ser
145                 150                 155                 160

Ser Ser Ser Pro Pro Glu Arg Arg Val Tyr Ser Trp Met Val Val Gly
                165                 170                 175

Asp Phe Asn Arg Ala Pro Ala Asn Leu Glu Val Ala Leu Arg Gln Glu
            180                 185                 190

Pro Ala Val Ser Glu Asn Thr Ile Ile Ile Ala Pro Thr Glu Pro Thr
        195                 200                 205

His Arg Ser Gly Asn Ile Leu Asp Tyr Ala Ile Leu His Asp Ala His
    210                 215                 220

Leu Pro Arg Arg Glu Gln Ala Arg Glu Arg Ile Gly Ala Ser Leu Met
225                 230                 235                 240

Leu Asn Gln Leu Arg Ser Gln Ile Thr Ser Asp His Phe Pro Val Ser
                245                 250                 255

Phe Val Arg Asp Arg
            260

<210> SEQ ID NO 2
<211> LENGTH: 255
<212> TYPE: PRT
<213> ORGANISM: Bacillus anthracis

<400> SEQUENCE: 2

Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu

```
            50                  55                  60
Lys Val Pro Ser Asp Val Leu Glu Met Tyr Lys Ala Ile Gly Gly Lys
 65                  70                  75                  80

Ile Tyr Ile Val Asp Gly Asp Ile Thr Lys His Ile Ser Leu Glu Ala
                 85                  90                  95

Leu Ser Glu Asp Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
            115                 120                 125

Leu Val Ile Gln Ser Ser Glu Asp Tyr Val Glu Asn Thr Glu Lys Ala
            130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
                180                 185                 190

Gln Leu Lys Glu His Pro Thr Asp Phe Ser Val Glu Phe Leu Glu Gln
            195                 200                 205

Asn Ser Asn Glu Val Gln Glu Val Phe Ala Lys Ala Phe Ala Tyr Tyr
            210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser
                245                 250                 255

<210> SEQ ID NO 3
<211> LENGTH: 527
<212> TYPE: PRT
<213> ORGANISM: Artificial Sequence
<220> FEATURE:
<223> OTHER INFORMATION: Synthetic

<400> SEQUENCE: 3

Ala Gly Gly His Gly Asp Val Gly Met His Val Lys Glu Lys Glu Lys
 1               5                  10                  15

Asn Lys Asp Glu Asn Lys Arg Lys Asp Glu Glu Arg Asn Lys Thr Gln
                20                  25                  30

Glu Glu His Leu Lys Glu Ile Met Lys His Ile Val Lys Ile Glu Val
            35                  40                  45

Lys Gly Glu Glu Ala Val Lys Lys Glu Ala Ala Glu Lys Leu Leu Glu
 50                  55                  60

Lys Val Pro Ser Asp Val Leu Glu Met Tyr Lys Ala Ile Gly Gly Lys
 65                  70                  75                  80

Ile Tyr Ile Val Asp Gly Asp Ile Thr Lys His Ile Ser Leu Glu Ala
                 85                  90                  95

Leu Ser Glu Asp Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
            115                 120                 125

Leu Val Ile Gln Ser Ser Glu Asp Tyr Val Glu Asn Thr Glu Lys Ala
            130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
```

```
            165                 170                 175
Ile Lys Asn Ala Ser Asp Ser Asp Gly Gln Asp Leu Leu Phe Thr Asn
                180                 185                 190
Gln Leu Lys Glu His Pro Thr Asp Phe Ser Val Glu Phe Leu Glu Gln
            195                 200                 205
Asn Ser Asn Glu Val Gln Glu Val Phe Ala Lys Ala Phe Ala Tyr Tyr
        210                 215                 220
Ile Glu Pro Gln His Arg Asp Val Leu Gln Leu Tyr Ala Pro Glu Ala
225                 230                 235                 240
Phe Asn Tyr Met Asp Lys Phe Asn Glu Gln Glu Ile Asn Leu Ser Thr
                245                 250                 255
Arg Ser Gly Glu Asn Leu Tyr Phe Gln Ser Asn Leu Ser Asp Phe Lys
            260                 265                 270
Val Ala Thr Trp Asn Leu Gln Gly Ser Ser Ala Val Asn Glu Ser Lys
        275                 280                 285
Trp Asn Ile Asn Val Arg Gln Leu Leu Ser Gly Glu Gln Gly Ala Asp
        290                 295                 300
Ile Leu Met Val Gln Glu Ala Gly Ser Leu Pro Ser Ser Ala Val Arg
305                 310                 315                 320
Thr Ser Arg Val Ile Gln His Gly Gly Thr Pro Ile Glu Glu Tyr Thr
                325                 330                 335
Trp Asn Leu Gly Thr Arg Ser Arg Pro Asn Met Val Tyr Ile Tyr Tyr
            340                 345                 350
Ser Arg Leu Asp Val Gly Ala Asn Arg Val Asn Leu Ala Ile Val Ser
            355                 360                 365
Arg Arg Gln Ala Asp Glu Ala Phe Ile Val His Ser Asp Ser Ser Val
        370                 375                 380
Leu Gln Ser Arg Pro Ala Val Gly Ile Arg Ile Gly Thr Asp Val Phe
385                 390                 395                 400
Phe Thr Val His Ala Leu Ala Thr Gly Gly Ser Asp Ala Val Ser Leu
                405                 410                 415
Ile Arg Asn Ile Phe Thr Thr Phe Asn Ser Ser Ser Pro Pro Glu
            420                 425                 430
Arg Arg Val Tyr Ser Trp Met Val Val Gly Asp Phe Asn Arg Ala Pro
            435                 440                 445
Ala Asn Leu Glu Val Ala Leu Arg Gln Glu Pro Ala Val Ser Glu Asn
        450                 455                 460
Thr Ile Ile Ile Ala Pro Thr Glu Pro Thr His Arg Ser Gly Asn Ile
465                 470                 475                 480
Leu Asp Tyr Ala Ile Leu His Asp Ala His Leu Pro Arg Arg Glu Gln
                485                 490                 495
Ala Arg Glu Arg Ile Gly Ala Ser Leu Met Leu Asn Gln Leu Arg Ser
            500                 505                 510
Gln Ile Thr Ser Asp His Phe Pro Val Ser Phe Val Arg Asp Arg
            515                 520                 525

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Thr Arg Ser Gly Glu Asn Leu Tyr Phe Gln Ser
```

<210> SEQ ID NO 5
<211> LENGTH: 29
<212> TYPE: PRT
<213> ORGANISM: Artificial Sequence
<220> FEATURE:
<223> OTHER INFORMATION: Synthetic

<400> SEQUENCE: 5

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala
            20                  25

<210> SEQ ID NO 6
<211> LENGTH: 87
<212> TYPE: DNA
<213> ORGANISM: Artificial Sequence
<220> FEATURE:
<223> OTHER INFORMATION: Synthetic

<400> SEQUENCE: 6
atgaaaaaac gaaaagtgtt aataccatta atggcattgt ctacgatatt agtttcaagc    60
acaggtaatt tagaggtgat tcaggca                                        87

<210> SEQ ID NO 7
<211> LENGTH: 765
<212> TYPE: DNA
<213> ORGANISM: Artificial Sequence
<220> FEATURE:
<223> OTHER INFORMATION: Synthetic

<400> SEQUENCE: 7
gcgggcggtc atggtgatgt aggtatgcac gtaaaagaga agagaaaaa taaagatgag     60 aataagagaa agatgaaga acgaaataaa acacaggaag agcatttaaa ggaaatcatg    120
aaacacattg taaaaataga agtaaaaggg gaggaagctg ttaaaaaaga ggcagcagaa    180
aagctacttg agaaagtacc atctgatgtt ttagagatgt ataaagcaat ggaggaaag    240 atatatattg tggatggtga tattacaaaa catatatctt tagaagcatt atctgaagat    300
aagaaaaaaa taaagacat ttatgggaaa gatgctttat tacatgaaca ttatgtatat    360
gcaaaagaag gatatgaacc cgtacttgta atccaatctt cggaagatta tgtagaaaat    420
actgaaaagg cactgaacgt ttattatgaa ataggtaaga tattatcaag ggatatttta    480
agtaaaatta tcaaccata tcagaaattt ttagatgtat aaataccat taaaaatgca     540 tctgattcag atggacaaga tcttttattt actaatcagc ttaaggaaca tcccacagac    600
ttttctgtag aattcttgga caaaatagc aatgaggtac aagaagtatt tgcgaaagct    660
tttgcatatt atatcgagcc acagcatcgt gatgttttac agctttatgc accggaagct    720
tttaattaca tggataaatt taacgaacaa gaaataaatc tatcc                    765

<210> SEQ ID NO 8
<211> LENGTH: 783
<212> TYPE: DNA
<213> ORGANISM: Artificial Sequence
<220> FEATURE:
<223> OTHER INFORMATION: Synthetic

<400> SEQUENCE: 8
aacttgagtg acttcaaagt agcaacttgg aatctgcaag gttcttcagc agtaaatgaa    60

```
agtaaatgga atattaatgt gcgccaatta ttatcgggag aacaaggtgc agatattttg    120
atggtacaag aagcgggttc cttaccaagt tcggcagtaa gaacctcacg ggtaattcaa    180
catgggggaa cgccaattga ggaatatact tggaatttag gtactcgttc ccgcccaaat    240
atggtctata tttattattc tcgtttagat gttggggcaa accgagtgaa cttagctatc    300
gtgtcacgcc gtcaagccga tgaagctttt atcgtacatt ctgattcttc tgtgcttcaa    360
tctcgccctg cagtaggtat ccgcattggt actgatgtat tttttacagt gcatgctttg    420
gccacaggcg ttctgatgc ggtaagtctg attcgtaata tcttcactac ttttaactca    480
tcatcatccc caccggaaag acgagtatat agctggatgg ttgttggtga tttcaatcgt    540
gcgccggcta atctggaagt tgcattaaga caggagcccg cagtgagtga aaatacaatt    600
attattgcgc caacagaacc gactcatcga tctggtaata ttttagatta tgcaatttta    660
catgatgcac atttaccacg tagagaacag gcccgtgaac gtatcggtgc aagtttaatg    720
ttaaatcagt tacgctcaca aattacatcc gatcattttc ctgttagttt tgttcgtgat    780
cgc                                                                 783

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
acgcgttccg gagagaatct ttattttcaa tca                                 33

<210> SEQ ID NO 10
<211> LENGTH: 776
<212> TYPE: PRT
<213> ORGANISM: Bacillus anthracis

<400> SEQUENCE: 10

Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175
```

```
Ile Lys Asn Ala Ser Asp Ser Asp Gly Gln Asp Leu Leu Phe Thr Asn
        180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
        210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg Met Leu Ser Arg Tyr Glu Lys Trp Glu
        260                 265                 270

Lys Ile Lys Gln His Tyr Gln His Trp Ser Asp Ser Leu Ser Glu Glu
        275                 280                 285

Gly Arg Gly Leu Leu Lys Lys Leu Gln Ile Pro Ile Glu Pro Lys Lys
        290                 295                 300

Asp Asp Ile Ile His Ser Leu Ser Gln Glu Glu Lys Glu Leu Leu Lys
305                 310                 315                 320

Arg Ile Gln Ile Asp Ser Ser Asp Phe Leu Ser Thr Glu Glu Lys Glu
                325                 330                 335

Phe Leu Lys Lys Leu Gln Ile Asp Ile Arg Asp Ser Leu Ser Glu Glu
        340                 345                 350

Glu Lys Glu Leu Leu Asn Arg Ile Gln Val Asp Ser Ser Asn Pro Leu
        355                 360                 365

Ser Glu Lys Glu Lys Glu Phe Leu Lys Lys Leu Lys Leu Asp Ile Gln
        370                 375                 380

Pro Tyr Asp Ile Asn Gln Arg Leu Gln Asp Thr Gly Gly Leu Ile Asp
385                 390                 395                 400

Ser Pro Ser Ile Asn Leu Asp Val Arg Lys Gln Tyr Lys Arg Asp Ile
                405                 410                 415

Gln Asn Ile Asp Ala Leu Leu His Gln Ser Ile Gly Ser Thr Leu Tyr
        420                 425                 430

Asn Lys Ile Tyr Leu Tyr Glu Asn Met Asn Ile Asn Asn Leu Thr Ala
        435                 440                 445

Thr Leu Gly Ala Asp Leu Val Asp Ser Thr Asp Asn Thr Lys Ile Asn
450                 455                 460

Arg Gly Ile Phe Asn Glu Phe Lys Lys Asn Phe Lys Tyr Ser Ile Ser
465                 470                 475                 480

Ser Asn Tyr Met Ile Val Asp Ile Asn Glu Arg Pro Ala Leu Asp Asn
                485                 490                 495

Glu Arg Leu Lys Trp Arg Ile Gln Leu Ser Pro Asp Thr Arg Ala Gly
        500                 505                 510

Tyr Leu Glu Asn Gly Lys Leu Ile Leu Gln Arg Asn Ile Gly Leu Glu
        515                 520                 525

Ile Lys Asp Val Gln Ile Ile Lys Gln Ser Glu Lys Glu Tyr Ile Arg
        530                 535                 540

Ile Asp Ala Lys Val Val Pro Lys Ser Lys Ile Asp Thr Lys Ile Gln
545                 550                 555                 560

Glu Ala Gln Leu Asn Ile Asn Gln Glu Trp Asn Lys Ala Leu Gly Leu
                565                 570                 575

Pro Lys Tyr Thr Lys Leu Ile Thr Phe Asn Val His Asn Arg Tyr Ala
        580                 585                 590
```

```
Ser Asn Ile Val Glu Ser Ala Tyr Leu Ile Leu Asn Glu Trp Lys Asn
            595                 600                 605

Asn Ile Gln Ser Asp Leu Ile Lys Lys Val Thr Asn Tyr Leu Val Asp
610                 615                 620

Gly Asn Gly Arg Phe Val Phe Thr Asp Ile Thr Leu Pro Asn Ile Ala
625                 630                 635                 640

Glu Gln Tyr Thr His Gln Asp Glu Ile Tyr Glu Gln Val His Ser Lys
            645                 650                 655

Gly Leu Tyr Val Pro Glu Ser Arg Ser Ile Leu Leu His Gly Pro Ser
            660                 665                 670

Lys Gly Val Glu Leu Arg Asn Asp Ser Glu Gly Phe Ile His Glu Phe
            675                 680                 685

Gly His Ala Val Asp Asp Tyr Ala Gly Tyr Leu Leu Asp Lys Asn Gln
            690                 695                 700

Ser Asp Leu Val Thr Asn Ser Lys Lys Phe Ile Asp Ile Phe Lys Glu
705                 710                 715                 720

Glu Gly Ser Asn Leu Thr Ser Tyr Gly Arg Thr Asn Glu Ala Glu Phe
            725                 730                 735

Phe Ala Glu Ala Phe Arg Leu Met His Ser Thr Asp His Ala Glu Arg
            740                 745                 750

Leu Lys Val Gln Lys Asn Ala Pro Lys Thr Phe Gln Phe Ile Asn Asp
            755                 760                 765

Gln Ile Lys Phe Ile Ile Asn Ser
            770                 775

<210> SEQ ID NO 11
<211> LENGTH: 269
<212> TYPE: PRT
<213> ORGANISM: Escherichia coli

<400> SEQUENCE: 11

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
    50                  55                  60

Ser Pro Pro Ser Thr Ala Val Asp Thr Gly Arg Val Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Phe Gly Gly
            100                 105                 110

Arg Val Asn Leu Ala Leu Val Ser Asn Arg Gln Ala Asp Glu Val Phe
        115                 120                 125

Val Leu Arg Pro Val Arg Gln Gly Gly Arg Pro Leu Leu Gly Ile Arg
    130                 135                 140

Ile Gly Asn Asp Ala Phe Phe Thr Ala His Ala Ile Ala Thr Arg Asn
145                 150                 155                 160

Asn Asp Ala Pro Ala Leu Val Glu Glu Val Tyr Ser Phe Phe Arg Asp
                165                 170                 175

Ser Arg Asp Pro Val His Gln Ala Ile Asn Trp Met Ile Leu Gly Asp
            180                 185                 190
```

```
Phe Asn Arg Glu Pro Asp Asp Leu Glu Val Asn Leu Thr Val Pro Val
        195                 200                 205

Arg Asn Ala Ser Glu Ile Ile Phe Pro Ala Ala Pro Thr Gln Thr Ser
    210                 215                 220

Gln Arg Thr Leu Asp Tyr Ala Val Ala Gly Asn Ala Val Ala Phe Arg
225                 230                 235                 240

Pro Phe Pro Leu Gln Ala Gly Ile Val Tyr Gly Ala Arg Arg Thr Gln
                245                 250                 255

Met Ser Ser Asp His Tyr Pro Val Gly Val Ser Arg Arg
                260                 265

<210> SEQ ID NO 12
<211> LENGTH: 283
<212> TYPE: PRT
<213> ORGANISM: Actinobacillus sp.

<400> SEQUENCE: 12

Met Gln Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
                20                  25                  30

Asn Leu Gln Gly Ser Ser Ala Val Asn Glu Ser Lys Trp Asn Ile Asn
            35                  40                  45

Val Arg Gln Leu Leu Ser Gly Glu Gln Gly Ala Asp Ile Leu Met Val
    50                  55                  60

Gln Glu Ala Gly Ser Leu Pro Ser Ser Ala Val Arg Thr Ser Arg Val
65                  70                  75                  80

Ile Gln His Gly Gly Thr Pro Ile Glu Glu Tyr Thr Trp Asn Leu Gly
                85                  90                  95

Thr Arg Ser Arg Pro Asn Met Val Tyr Ile Tyr Tyr Ser Arg Leu Asp
                100                 105                 110

Val Gly Ala Asn Arg Val Asn Leu Ala Ile Val Ser Arg Arg Gln Ala
            115                 120                 125

Asp Glu Ala Phe Ile Val His Ser Asp Ser Ser Val Leu Gln Ser Arg
130                 135                 140

Pro Ala Val Gly Ile Arg Ile Gly Thr Asp Val Phe Phe Thr Val His
145                 150                 155                 160

Ala Leu Ala Thr Gly Gly Ser Asp Ala Val Ser Leu Ile Arg Asn Ile
                165                 170                 175

Phe Thr Thr Phe Thr Ser Ser Pro Ser Ser Pro Glu Arg Arg Gly Tyr
            180                 185                 190

Ser Trp Met Val Val Gly Asp Phe Asn Arg Ala Pro Val Asn Leu Glu
    195                 200                 205

Ala Ala Leu Arg Gln Glu Pro Ala Val Ser Glu Asn Thr Ile Ile Ile
210                 215                 220

Ala Pro Thr Glu Pro Thr His Arg Ser Gly Asn Ile Leu Asp Tyr Ala
225                 230                 235                 240

Ile Leu His Asp Ala His Leu Pro Arg Arg Glu Gln Ala Arg Glu Arg
                245                 250                 255

Ile Gly Ala Ser Leu Met Leu Asn Gln Leu Arg Ser Gln Ile Thr Ser
            260                 265                 270

Asp His Phe Pro Val Ser Phe Val His Asp Arg
                275                 280
```

<210> SEQ ID NO 13
<211> LENGTH: 265
<212> TYPE: PRT
<213> ORGANISM: Campylobacter jejuni

<400> SEQUENCE: 13

Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
        35                  40                  45

Gly Ala Asn Pro Leu Asp Ile Leu Met Ile Gln Glu Ala Gly Thr Leu
    50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Glu Val Ile Val Leu
        115                 120                 125

Pro Pro Pro Thr Thr Val Ser Arg Pro Ile Ile Gly Ile Arg Asn Gly
    130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
            260                 265

<210> SEQ ID NO 14
<211> LENGTH: 283
<212> TYPE: PRT
<213> ORGANISM: Aggregatibacter actinomycetemcomitans

<400> SEQUENCE: 14

Met Gln Trp Val Lys Gln Leu Asn Val Val Phe Cys Thr Met Leu Phe
1               5                   10                  15

Ser Phe Ser Ser Tyr Ala Asn Leu Ser Asp Phe Lys Val Ala Thr Trp
            20                  25                  30

Asn Leu Gln Gly Ser Ser Ala Val Asn Glu Ser Lys Trp Asn Ile Asn
        35                  40                  45

Val Arg Gln Leu Leu Ser Gly Glu Gly Ala Asp Ile Leu Met Val
    50                  55                  60

Gln Glu Ala Gly Ser Leu Pro Ser Ser Ala Val Arg Thr Ser Arg Val

```
                65                  70                  75                  80
        Ile Gln His Gly Gly Thr Pro Ile Glu Glu Tyr Thr Trp Asn Leu Gly
                        85                  90                  95

Thr Arg Ser Arg Pro Asn Met Val Tyr Ile Tyr Tyr Ser Arg Leu Asp
                        100                 105                 110

Val Gly Ala Asn Arg Val Asn Leu Ala Ile Val Ser Arg Arg Gln Ala
                        115                 120                 125

Asp Glu Ala Phe Ile Val His Ser Asp Ser Val Leu Gln Ser Arg
                        130                 135                 140

Pro Ala Val Gly Ile Arg Ile Gly Thr Asp Val Phe Phe Thr Val His
        145                 150                 155                 160

Ala Leu Ala Thr Gly Gly Ser Asp Ala Val Ser Leu Ile Arg Asn Ile
                        165                 170                 175

Phe Thr Thr Phe Thr Ser Ser Pro Ser Ser Pro Glu Arg Arg Gly Tyr
                        180                 185                 190

Ser Trp Met Val Val Gly Asp Phe Asn Arg Ala Pro Val Asn Leu Glu
                        195                 200                 205

Ala Ala Leu Arg Gln Glu Pro Ala Val Ser Glu Asn Thr Ile Ile Ile
                        210                 215                 220

Ala Pro Thr Glu Pro Thr His Arg Ser Gly Asn Ile Leu Asp Tyr Ala
        225                 230                 235                 240

Ile Leu His Asp Ala His Leu Pro Arg Arg Glu Gln Ala Arg Glu Arg
                        245                 250                 255

Ile Gly Ala Ser Leu Met Leu Asn Gln Leu Arg Ser Gln Ile Thr Ser
                        260                 265                 270

Asp His Phe Pro Val Ser Phe Val Arg Asp Arg
                        275                 280

<210> SEQ ID NO 15
<211> LENGTH: 269
<212> TYPE: PRT
<213> ORGANISM: Salmonella enterica subsp. enterica serovar Typhi

<400> SEQUENCE: 15

Met Lys Lys Pro Val Phe Phe Leu Leu Thr Met Ile Ile Cys Ser Tyr
        1               5                   10                  15

Ile Ser Phe Ala Cys Ala Asn Ile Ser Asp Tyr Lys Val Met Thr Trp
                        20                  25                  30

Asn Leu Gln Gly Ser Ser Ala Ser Thr Glu Ser Lys Trp Asn Val Asn
                        35                  40                  45

Val Arg Gln Leu Leu Ser Gly Thr Ala Gly Val Asp Ile Leu Met Val
                        50                  55                  60

Gln Glu Ala Gly Ala Val Pro Thr Ser Ala Val Pro Thr Gly Arg His
        65                  70                  75                  80

Ile Gln Pro Phe Gly Val Gly Ile Pro Ile Asp Glu Tyr Thr Trp Asn
                        85                  90                  95

Leu Gly Thr Thr Ser Arg Gln Asp Ile Arg Tyr Ile Tyr His Ser Ala
                        100                 105                 110

Ile Asp Val Gly Ala Arg Arg Val Asn Leu Ala Ile Val Ser Arg Gln
                        115                 120                 125

Arg Ala Asp Asn Val Tyr Val Leu Arg Pro Thr Thr Val Ala Ser Arg
                        130                 135                 140

Pro Val Ile Gly Ile Gly Leu Gly Asn Asp Val Phe Leu Thr Ala His
        145                 150                 155                 160
```

```
Ala Leu Ala Ser Gly Gly Pro Asp Ala Ala Ile Val Arg Val Thr
            165                 170                 175

Ile Asn Phe Phe Arg Gln Pro Gln Met Arg His Leu Ser Trp Phe Leu
        180                 185                 190

Ala Gly Asp Phe Asn Arg Ser Pro Asp Arg Leu Glu Asn Asp Leu Met
            195                 200                 205

Thr Glu His Leu Glu Arg Val Val Ala Val Leu Ala Pro Thr Glu Pro
    210                 215                 220

Thr Gln Ile Gly Gly Ile Leu Asp Tyr Gly Val Ile Val Asp Arg
225                 230                 235                 240

Ala Pro Tyr Ser Gln Arg Val Glu Ala Leu Arg Asn Pro Gln Leu Ala
            245                 250                 255

Ser Asp His Tyr Pro Val Ala Phe Leu Ala Arg Ser Cys
            260                 265

<210> SEQ ID NO 16
<211> LENGTH: 233
<212> TYPE: PRT
<213> ORGANISM: Helicobacter bilis

<400> SEQUENCE: 16

Ser Ser Ala Ser Thr Glu Asn Lys Trp Asn Val Ser Val Arg Gln Leu
1               5                   10                  15

Ile Thr Gly Asp Asn Pro Val Asp Ile Leu Met Val Gln Glu Ala Gly
            20                  25                  30

Ser Val Pro Thr Ser Ala Arg Pro Thr Gly Arg Met Ile Gln Pro Gly
        35                  40                  45

Gly Thr Pro Ile Gln Glu Tyr Val Trp Asp Leu Gly Thr Arg Ser Arg
    50                  55                  60

Pro Arg Ser Val Phe Ile Tyr Tyr Ala Asn Ile Asp Ala Gly Ala Arg
65                  70                  75                  80

Arg Val Asn Leu Ala Ile Val Ser Gly Arg Gln Ala Asp Glu Val Phe
                85                  90                  95

Val Ile Ser Gln Ser Thr Ile Ala Pro Glu Val Ser Arg Pro Val Ile
            100                 105                 110

Gly Ile Arg Leu Gly Asn Asp Val Phe Phe Asn Ile His Ala Leu Ala
        115                 120                 125

Arg Gly Gly Gly Asp Ala Ala Leu Val Thr Ala Val His Asp His
    130                 135                 140

Phe Val Gly Gln Pro Ser Ile Asn Trp Leu Ile Ala Gly Asp Phe Asn
145                 150                 155                 160

Arg Asp Pro Ala Asn Leu Leu Ser Gly Leu Asp Thr Arg Ile Thr Asn
                165                 170                 175

His Thr Arg Ile Val Thr Gln Asn Ser Ala Thr His Phe Ser Met Gly
            180                 185                 190

Ala Ala Asn Arg Ile Leu Asp Tyr Ala Ile Val Gly Arg Ser Ser Asn
        195                 200                 205

Asp Arg Ser Arg Leu Ala Leu Pro Thr Ile Thr Ala Leu Leu Met Ala
    210                 215                 220

Ala Ser Val Arg Ser His Leu Ser Ser
225                 230

<210> SEQ ID NO 17
<211> LENGTH: 269
<212> TYPE: PRT
<213> ORGANISM: Providencia alcalifaciens
```

<400> SEQUENCE: 17

```
Met Ile Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Ile Gln Glu Ala Gly
    50                  55                  60

Ser Pro Pro Ser Thr Ala Val Asp Thr Gly Arg Val Ile His Ser Pro
65                  70                  75                  80

Gly Ile Pro Ile Arg Glu Leu Ile Trp Asn Leu Ser Thr Asn Ser Arg
                85                  90                  95

Pro Glu Gln Val Tyr Ile Tyr Phe Ser Ala Val Asp Ala Leu Gly Gly
                100                 105                 110

Arg Val Asn Leu Ala Leu Ile Ser Asn Arg Arg Ala Asp Glu Val Phe
            115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Thr Arg Asn
145                 150                 155                 160

Asn Asp Ala Pro Ala Leu Val Glu Glu Val Tyr Asn Phe Phe Arg Asp
                165                 170                 175

Ser Arg Asp Pro Leu His Gln Ala Leu Asn Trp Met Ile Leu Gly Asp
            180                 185                 190

Phe Asn Arg Glu Pro Asp Asp Leu Glu Met Asn Leu Thr Val Pro Val
        195                 200                 205

Arg Asn Ala Ser Glu Ile Ile Phe Pro Ala Ala Thr Gln Thr Ser
    210                 215                 220

Gln Arg Thr Leu Asp Tyr Ala Val Ala Gly Asn Ala Val Ala Phe Arg
225                 230                 235                 240

Pro Leu Pro Leu Gln Ala Gly Ile Val Tyr Gly Ala Arg Arg Thr Gln
                245                 250                 255

Ile Ser Ser Asp His Tyr Pro Val Gly Val Phe Arg Arg
            260                 265
```